(12) United States Patent
Zhang et al.

(10) Patent No.: US 10,556,896 B2
(45) Date of Patent: Feb. 11, 2020

(54) **CRYSTALLINE FORMS OF (3-AMINO-OXETAN-3-YLMETHYL)-[2-(5,5-DIOXO-5,6,7,9-TETRAHYDRO-5LAMBDA\*6\*-THIA-8-AZA-BENZOCYCLOHEPTEN-8-YL)-6-METHYL-QUINAZOLIN-4-YL]-AMINE**

(71) Applicant: Hoffmann-La Roche Inc., Little Falls, NJ (US)

(72) Inventors: Wei Zhang, Shanghai (CN); Lin Wang, Shanghai (CN); Wei Li, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/058,684

(22) Filed: Aug. 8, 2018

(65) Prior Publication Data

US 2019/0092766 A1 Mar. 28, 2019

Related U.S. Application Data

(60) Division of application No. 15/870,151, filed on Jan. 12, 2018, now Pat. No. 10,071,999, which is a continuation of application No. PCT/EP2016/066482, filed on Jul. 12, 2016.

(51) Int. Cl.
| | |
|---|---|
| C07D 417/14 | (2006.01) |
| C07D 417/04 | (2006.01) |
| A61P 31/12 | (2006.01) |
| A61P 31/14 | (2006.01) |

(52) U.S. Cl.
CPC ............ *C07D 417/14* (2013.01); *A61P 31/12* (2018.01); *A61P 31/14* (2018.01); *C07D 417/04* (2013.01); *C07B 2200/13* (2013.01)

(58) Field of Classification Search
CPC .................................... C07D 417/14
USPC ..................................... 514/211.09
See application file for complete search history.

(56) References Cited

U.S. PATENT DOCUMENTS

| | | | |
|---|---|---|---|
| 10,071,999 B2 * | 9/2018 | Zhang | .......... C07D 417/04 |
| 2002/0099208 A1 | 7/2002 | Yu et al. | |

FOREIGN PATENT DOCUMENTS

| | | |
|---|---|---|
| DE | 2345064 A1 | 4/1974 |
| WO | 2005/061513 A1 | 7/2005 |
| WO | 2013/020993 A1 | 2/2013 |
| WO | 2013/053658 A1 | 4/2013 |
| WO | 2014/184163 A1 | 11/2014 |
| WO | 2015/110446 A1 | 7/2015 |

OTHER PUBLICATIONS

International Search Report for PCT/EP2012/065499 dated Sep. 28, 2012.
International Preliminary Report on Patentability issued in International Application No. PCT/EP2015/051066, dated Jul. 26, 2016, in 9 pages.
International Search Report issued in International Application No. PCT/EP2015/051066, dated Feb. 19, 2015, in 3 pages.
ISR and Written Opinion of PCT/EP2016/066482 (dated Jan. 4, 2017).
Written Opinion of the International Searching Authority issued in International Application No. PCT/EP2015/051066, dated Feb. 19, 2015, in 8 pages.

* cited by examiner

*Primary Examiner* — Kahsay Habte
(74) *Attorney, Agent, or Firm* — Mark D. Kafka

(57) ABSTRACT

The present invention relates to novel crystalline forms of compound (I),

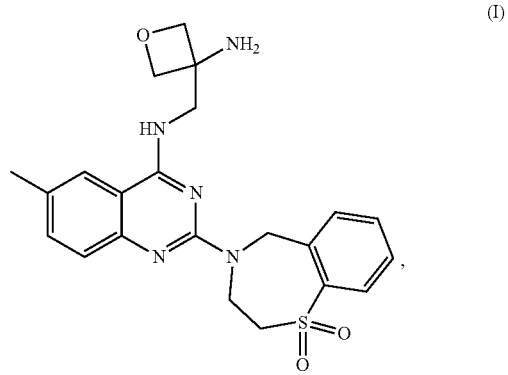

(3-Amino-oxetan-3-ylmethyl)-[2-(5,5-dioxo-5,6,7,9-tetrahydro-5lambda\*6\*-thia-8-aza-benzocyclohepten-8-yl)-6-methyl-quinazolin-4-yl]-amine and pharmaceutical compositions comprising the crystalline forms thereof disclosed herein, which may be used for the treatment or prophylaxis of a viral disease in a patient relating to respiratory syncytial virus (RSV) infection or a disease caused by RSV infection.

22 Claims, 20 Drawing Sheets

CRYSTALLINE FORMS OF (3-AMINO-OXETAN-3-YLMETHYL)-[2-(5,5-DIOXO-5,6,7,9-TETRAHYDRO-5LAMBDA*6*-THIA-8-AZA-BENZOCYCLOHEPTEN-8-YL)-6-METHYL-QUINAZOLIN-4-YL]-AMINE

CROSS-REFERENCE TO RELATED APPLICATIONS

This application is a division of U.S. patent application Ser. No. 15/870,151, filed on Jan. 12, 2018, which issued as U.S. Pat. No. 10,071,999 on Sep. 11, 2018, which is a continuation of International Patent Application No. PCT/EP2016/066482, filed on Jul. 12, 2016, which claims priority to International Patent Application No. PCT/CN2015/084225, filed on Jul. 16, 2015. The entire contents of each of the above patent applications are hereby incorporated by reference.

The present invention relates to novel crystalline forms of compound (I),

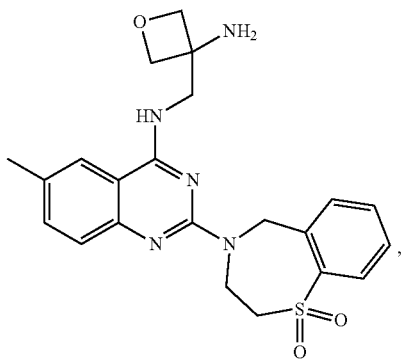

(I)

(3-Amino-oxetan-3-ylmethyl)-[2-(5,5-dioxo-5,6,7,9-tetrahydro-5lambda*6*-thia-8-aza-benzocyclohepten-8-yl)-6-methyl-quinazolin-4-yl]-amine (also named as N-[(3-Aminooxetan-3-yl)methyl]-2-(1,1-dioxido-2,3-dihydro-1,4-benzothiazepin-4(5H)-yl)-6-methylquinazolin-4-amine) and pharmaceutical compositions comprising the crystalline forms thereof disclosed herein, which may be used for the treatment or prophylaxis of a viral disease in a patient relating to respiratory syncytial virus (RSV) infection or a disease caused by RSV infection.

BACKGROUND OF THE INVENTION

Respiratory Syncytial Virus (RSV) is the leading viral cause of death in children less than 5 years old and pediatric lower respiratory tract infection and infant hospitalization. Elderly and immune compromised adults are also high risk population. Currently, there is no approved vaccine on the market. Inhibitors of RSV are useful to limit the establishment and progression of infection by RSV as well as in diagnostic assays for RSV.

(3-Amino-oxetan-3-ylmethyl)-[2-(5,5-dioxo-5,6,7,9-tetrahydro-5lambda*6*-thia-8-aza-benzocyclohepten-8-yl)-6-methyl-quinazolin-4-yl]-amine (compound (I)) was disclosed in WO2013020993 as an effective respiratory syncytial virus (RSV) inhibitor. The compound (I) is also named as N-[(3-Aminooxetan-3-yl)methyl]-2-(1,1-dioxido-2,3-dihydro-1,4-benzothiazepin-4(5H)-yl)-6-methylquinazolin-4-amine.

Form D of compound (I) was found as metastable form at the early research stage and the hygroscopicity of Form D of compound (I) makes it not suitable for further drug development. As an action of risk mitigation, comprehensive studies were conducted. As one of the objections of this patent, several novel crystalline forms were synthesized and characterized, showing significantly improved hygroscopicity compared with Form D of compound (I). Meanwhile, developing novel crystalline forms of compound (I) with good stability and/or aqueous solubility are also one of the objectives of this patent respectively. These novel crystalline forms enhanced the developability of compound (I) fundamentally.

The present disclosure relates generally to novel crystalline forms of compound (I), and processes to make those forms.

SUMMARY OF THE INVENTION

The present invention relates to polymorphs, salts, co-crystals and methods for the synthesis of selective production of crystalline forms of (3-Amino-oxetan-3-ylmethyl)-[2-(5,5-dioxo-5,6,7,9-tetrahydro-5lambda*6*-thia-8-aza-benzocyclohepten-8-yl)-6-methyl-quinazolin-4-yl]-amine.

In one aspect, the crystalline form of compound (I) is Form A, Form B, Form C, Form D, Form E or Form F or a combination thereof.

In another embodiment, the crystalline form of compound (I) is Form A that exhibits an X-ray powder diffraction (XRPD) pattern with characteristic peaks expressed in degrees 2-theta at 9.79°±0.10°, 10.64°±0.10°, 16.79°±0.10°, 17.51°±0.10°, 20.12°±0.10°, 21.62°±0.10° and 25.79°±0.10°.

In a further embodiment, the crystalline form of compound (I) is Form A that exhibits an X-ray powder diffraction (XRPD) pattern with characteristic peaks expressed in degrees 2-theta at 6.46°±0.10°, 8.37°±0.10°, 9.79°±0.10°, 10.64°±0.10°, 12.91°±0.10°, 16.79°±0.10°, 17.51°±0.10°, 18.15°±0.10°, 19.65°±0.10°, 20.12°±0.10°, 21.62°±0.10°, 23.34°±0.10° and 25.79°±0.10°.

In a further embodiment, the crystalline form of compound (I) is Form A that exhibits an X-ray powder diffraction (XRPD) pattern shown in FIG. 1.

In a further embodiment, the crystalline form of compound (I) is Form A with a differential scanning calorimetry (DSC) thermogram comprising endothermic peak with onset temperature at 225.3° C.±3° C.

In another embodiment, the crystalline form of compound (I) is Form B that exhibits an X-ray powder diffraction (XRPD) pattern with characteristic peaks expressed in degrees 2-theta at 10.21°±0.10°, 11.93°±0.10°, 13.22°±0.10°, 14.35°±0.10°, 18.56°±0.10°, 20.79°±0.10°, 23.24°±0.10° and 25.15°±0.10°.

In a further embodiment, the crystalline form of compound (I) is Form B that exhibits an X-ray powder diffraction (XRPD) pattern with characteristic peaks expressed in degrees 2-theta at 10.21°±0.10°, 11.93°±0.10°, 13.22°±0.10°, 14.35°±0.10°, 15.02°±0.10°, 16.31°±0.10°, 17.66°±0.10°, 18.56°±0.10°, 20.06°±0.10°, 20.79°±0.10°, 21.42°±0.10°, 23.24°±0.10°, 25.15°±0.10°, 26.21°±0.10°, 26.74°±0.10° and 29.44°±0.10°.

In a further embodiment, the crystalline form of compound (I) is Form B that exhibits an X-ray powder diffraction (XRPD) pattern shown in FIG. 4.

In a further embodiment, the crystalline Form B is a hydrate of compound (I).

In a further embodiment, the crystalline form of compound (I) is Form B with a differential scanning calorimetry (DSC) thermogram comprising endothermic peak with dehydration temperature at 57.2° C.±3° C. and onset temperature at 256.3° C.±3° C.

In another embodiment, the crystalline form of compound (I) is Form C that exhibits an X-ray powder diffraction (XRPD) pattern with characteristic peaks expressed in degrees 2-theta at 8.41°±0.10°, 19.21°±0.10°, 20.49°±0.10°, 20.83°±0.10°, 21.69°±0.10°, 21.99°±0.10° and 22.13°±0.10°.

In a further embodiment, the crystalline form of compound (I) is Form C that exhibits an X-ray powder diffraction (XRPD) pattern with characteristic peaks expressed in degrees 2-theta at 8.41°±0.10°, 13.71°±0.10°, 14.95°±0.10°, 17.01°±0.10°, 19.21°±0.10°, 20.49°±0.10°, 20.83°±0.10°, 21.46°±0.10°, 21.69°±0.10°, 21.99°±0.10°, 22.13°±0.10°, 24.95°±0.10°, 25.85°±0.10°, 26.63°±0.10° and 27.34°±0.10°.

In a further embodiment, the crystalline form of compound (I) is Form C that exhibits an X-ray powder diffraction (XRPD) pattern shown in FIG. 7.

In a further embodiment, the crystalline form of compound (I) is Form C with a differential scanning calorimetry (DSC) thermogram comprising endothermic peak with onset temperature at 256.6° C.±3° C.

In another embodiment, the crystalline form of compound (I) is Form D that exhibits an X-ray powder diffraction (XRPD) pattern with characteristic peaks expressed in degrees 2-theta at 7.79°±0.10°, 10.18°±0.10°, 11.15°±0.10°, 12.40°±0.10°, 18.68°±0.10°, 20.43°±0.10° and 24.83°±0.10°.

In a further embodiment, the crystalline form of compound (I) is Form D that exhibits an X-ray powder diffraction (XRPD) pattern with characteristic peaks expressed in degrees 2-theta at 7.79°±0.10°, 10.18°±0.10°, 11.15°±0.10°, 12.40°±0.10°, 12.90°±0.10°, 18.68°±0.10°, 19.73°±0.10°, 20.16°±0.10°, 20.43°±0.10°, 21.16°±0.10°, 23.14°±0.10°, 23.93°±0.10°, 24.83°±0.10°, 25.71°±0.10° and 27.11°±0.10°.

In a further embodiment, the crystalline form of compound (I) is Form D that exhibits an X-ray powder diffraction (XRPD) pattern shown in FIG. 11.

In a further embodiment, the crystalline form of compound (I) is Form D with a differential scanning calorimetry (DSC) thermogram comprising endothermic peak with dehydration temperature at 53.2° C.±3° C. and onset melting temperature at 256.3° C.±3° C.

In another embodiment, the crystalline form of compound (I) is Form E that exhibits an X-ray powder diffraction (XRPD) pattern with characteristic peaks expressed in degrees 2-theta at 5.96°±0.10°, 8.32°±0.10°, 9.34°±0.10°, 11.82°±0.10°, 15.09°±0.10°, 19.44°±0.10° and 25.60°±0.10°.

In a further embodiment, the crystalline form of compound (I) is Form E that exhibits an X-ray powder diffraction (XRPD) pattern with characteristic peaks expressed in degrees 2-theta at 5.96°±0.10°, 8.32°±0.10°, 9.34°±0.10°, 11.82°±0.10°, 13.22°±0.10°, 15.09°±0.10°, 16.90°±0.10°, 17.46°±0.10°, 19.44°±0.10°, 21.08°±0.10°, 22.59°±0.10°, 23.12°±0.10°, 25.25°±0.10°, 25.60°±0.10° and 28.34°±0.10°.

In a further embodiment, the crystalline form of compound (I) is Form E that exhibits an X-ray powder diffraction (XRPD) pattern shown in FIG. 14.

In a further embodiment, the crystalline Form E is a mono acetate salt of compound (I).

In another embodiment, the crystalline form of compound (I) is Form F that exhibits an X-ray powder diffraction (XRPD) pattern with characteristic peaks expressed in degrees 2-theta at 10.27°±0.10°, 12.38°±0.10°, 18.59°±0.10°, 19.91°±0.10°, 20.14°±0.10°, 23.93°±0.10° and 24.78°±0.10°.

In a further embodiment, the crystalline form of compound (I) is Form F that exhibits an X-ray powder diffraction (XRPD) pattern with characteristic peaks expressed in degrees 2-theta at 8.32°±0.10°, 10.27°±0.10°, 12.38°±0.10°, 13.05°±0.10°, 16.58°±0.10°, 18.01°±0.10°, 18.59°±0.10°, 19.70°±0.10°, 19.91°±0.10°, 20.14°±0.10°, 22.01°±0.10°, 23.56°±0.10°, 23.93°±0.10°, 24.78°±0.10° and 26.39°±0.10°.

In a further embodiment, the crystalline form of compound (I) is Form F that exhibits an X-ray powder diffraction (XRPD) pattern shown in FIG. 15.

In a further embodiment, the crystalline Form F is a mono maleic salt of compound (I).

In another aspect, provided herein is a pharmaceutical composition comprising the crystalline form disclosed herein; and a pharmaceutically acceptable carrier, excipient, diluent, adjuvant, vehicle or a combination thereof.

In another aspect, provided herein is the use of the amorphous or crystalline form disclosed herein or the pharmaceutical composition for the manufacture of a medicament for the treatment or prophylaxis of a viral disease in a patient.

In another aspect, the viral disease disclosed herein is respiratory syncytial virus infection or a disease caused by respiratory syncytial virus infection.

In another aspect, provided herein is a method for the treatment or prophylaxis of respiratory syncytial virus infection or a disease caused by respiratory syncytial virus infection, which method comprises administering a therapeutically effective amount of the crystalline form or the pharmaceutical composition disclosed herein.

ABBREVIATIONS

DSC Differential scanning calorimetry
DVS Dynamic vapor sorption
Pos. Position
Rel. Int. Relative Intensity
TGA Thermal gravimetric analysis
XRPD X-ray powder diffraction
SGF Simulated Gastric Fluid
FaSSIF Fasted State Simulated Intestinal Fluid
FeSSIF Fed State Simulated Intestinal Fluid

EXAMPLES

The invention will be more fully understood by reference to the following examples. They should not, however, be construed as limiting the scope of the invention.

HPLC Method for Chemical Purity and Assay Test

HPLC condition is disclosed here in Table 1-1.

TABLE 1-1

HPLC conditions for chemical purity and assay test

| Instrument | Agilent 1200 series HPLC system with DAD detector |
| Column | Waters Xbridge Shield RP18(150 × 4.6 mm, 3.5 μm) |
| Oven temperature | 40° C. |
| Mobile phase | A: 0.1% $NH_3 \cdot H_2O$ in water |
|  | B: 0.1% $NH_3 \cdot H_2O$ in Acetonitrile |

| | Time (min) | A % | B % |
|---|---|---|---|
| Gradient program | 0.00 | 88 | 12 |
| | 2.00 | 65 | 35 |
| | 10.00 | 55 | 45 |
| | 20.00 | 0 | 100 |
| | 23.00 | 0 | 100 |
| | 23.01 | 88 | 12 |
| | 28.00 | 88 | 12 |

| Flow rate | 0.8 mL/min |
| Detector | UV 238 nm |
| Injection Volume | 10 μL |
| Diluent | Acetonitrile:Water = 1:1, v/v |

Example 1

Preparation of Form A of Compound (I)

100 mg of amorphous compound (I) was weighed and transferred into a solvent mixture (MeOH:$H_2O$ (1:5)). Then the precipitation was collected by filtration and the collected solid was thoroughly washed with water and dried under vacuum to get a white solid as Form A.

Figure 1:
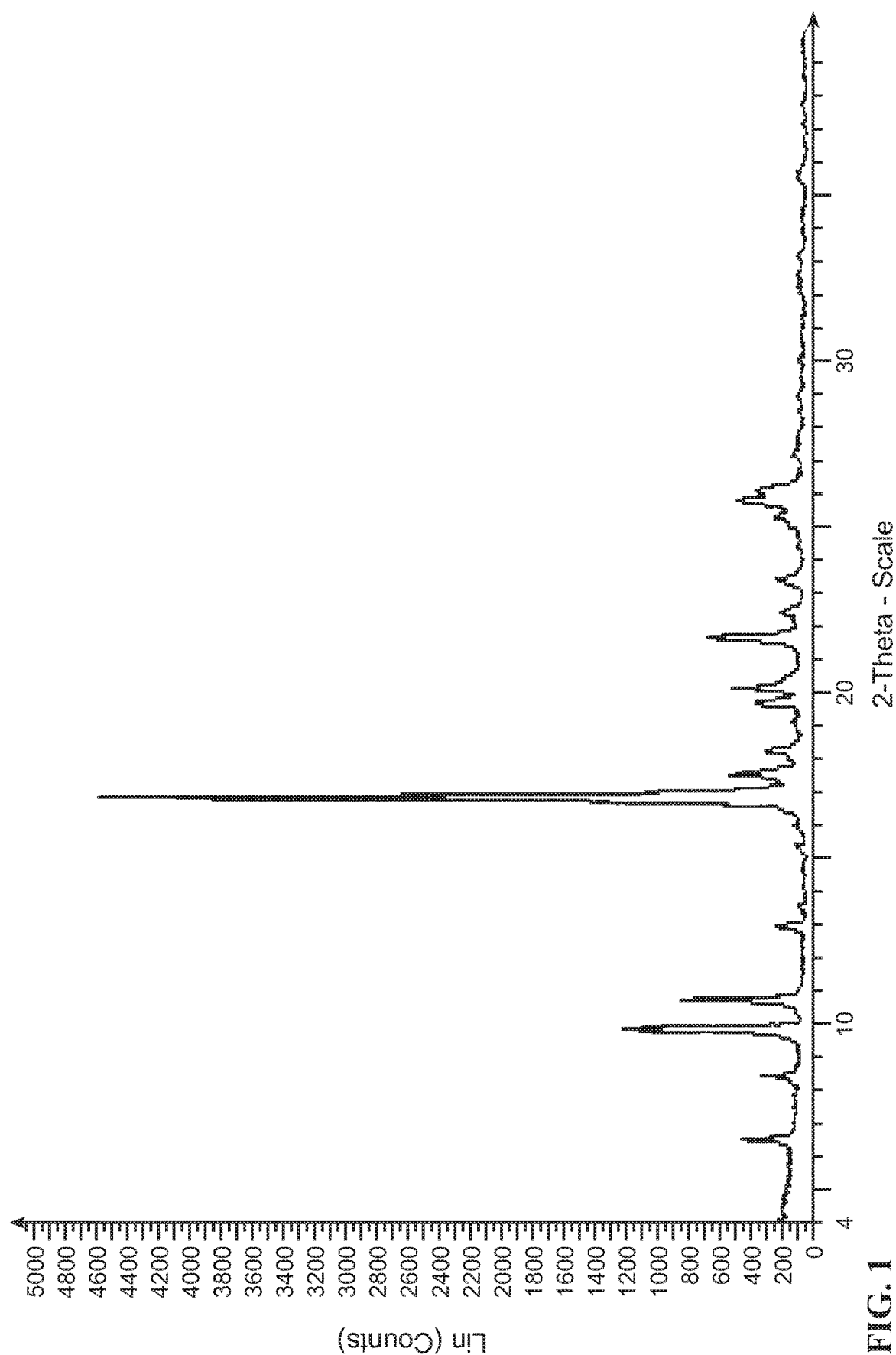
FIG. 1 X-ray powder diffraction pattern for Form A
FIG. 2 DSC thermogram of Form A
FIG. 3 TGA diagram of Form A
FIG. 4 X-ray powder diffraction pattern for Form B
FIG. 5 DSC thermogram of Form B
FIG. 6 TGA diagram of Form B
FIG. 7 X-ray powder diffraction pattern for Form C
FIG. 8 DSC thermogram of Form C
FIG. 9 TGA diagram of Form C
FIG. 10 X-ray crystal structure of Form C
FIG. 11 X-ray powder diffraction pattern for Form D
FIG. 12 DSC thermogram of Form D
FIG. 13 TGA diagram of Form D
FIG. 14 X-ray powder diffraction pattern for mono acetate salt Form E
FIG. 15 X-ray powder diffraction pattern for mono maleic salt Form F FIG. 16 DVS isotherm of Form A
FIG. 17 DVS isotherm of Form C
FIG. 18 DVS isotherm of Form D
FIG. 19 DVS isotherm of mono acetate salt Form E
FIG. 20 DVS isotherm of mono maleic salt Form F

Form A was analysed using XRPD. The XRPD pattern is shown in FIG. 1. Major peaks and their related intensities in the XRPD pattern are shown in Table 1.

Experimental Conditions:

XRPD: For crystalline form analysis, sample was mounted in a sample holder on a goniometer and measured at ambient conditions. Data were collected at 2-theta from 4 to 40° with a step size of 0.05° and a scanning speed of is/step on a Bruker D8 Advance X-ray powder diffractometer at 40 KV and 40 mA. Cu-radiation of 1.54 Å wavelength was used for data collection.

DSC analysis: DSC curves were recorded using a TA differential scanning calorimeter Q2000. The sample was heated from 25° C. to 350° C. at a rate of 10° C./min.

TGA analysis: The thermogravimetric analysis was operated on TA Q5000. The sample was heated from 120° C. to 400° C. at a rate of 10° C./min.

TABLE 1

X-Ray Powder Diffraction peaks of Form A of compound (I)

| Pos. [°2 Th.] | Height [cts] | d-spacing [Å] | Rel. Int. [%] |
|---|---|---|---|
| 6.46 | 454 | 13.6799 | 9.9 |
| 8.37 | 282 | 10.5505 | 6.1 |
| 9.79 | 1219 | 9.0291 | 26.5 |
| 10.64 | 856 | 8.3119 | 18.6 |
| 12.91 | 241 | 6.8499 | 5.2 |
| 16.79 | 4595 | 5.2750 | 100.0 |
| 17.51 | 539 | 5.0602 | 11.7 |
| 18.15 | 275 | 4.8842 | 6.0 |
| 19.65 | 371 | 4.5147 | 8.1 |
| 20.12 | 524 | 4.4109 | 11.4 |
| 21.62 | 676 | 4.1072 | 14.7 |
| 23.34 | 221 | 3.8079 | 4.8 |
| 25.79 | 485 | 3.4515 | 10.6 |

Figure 2:
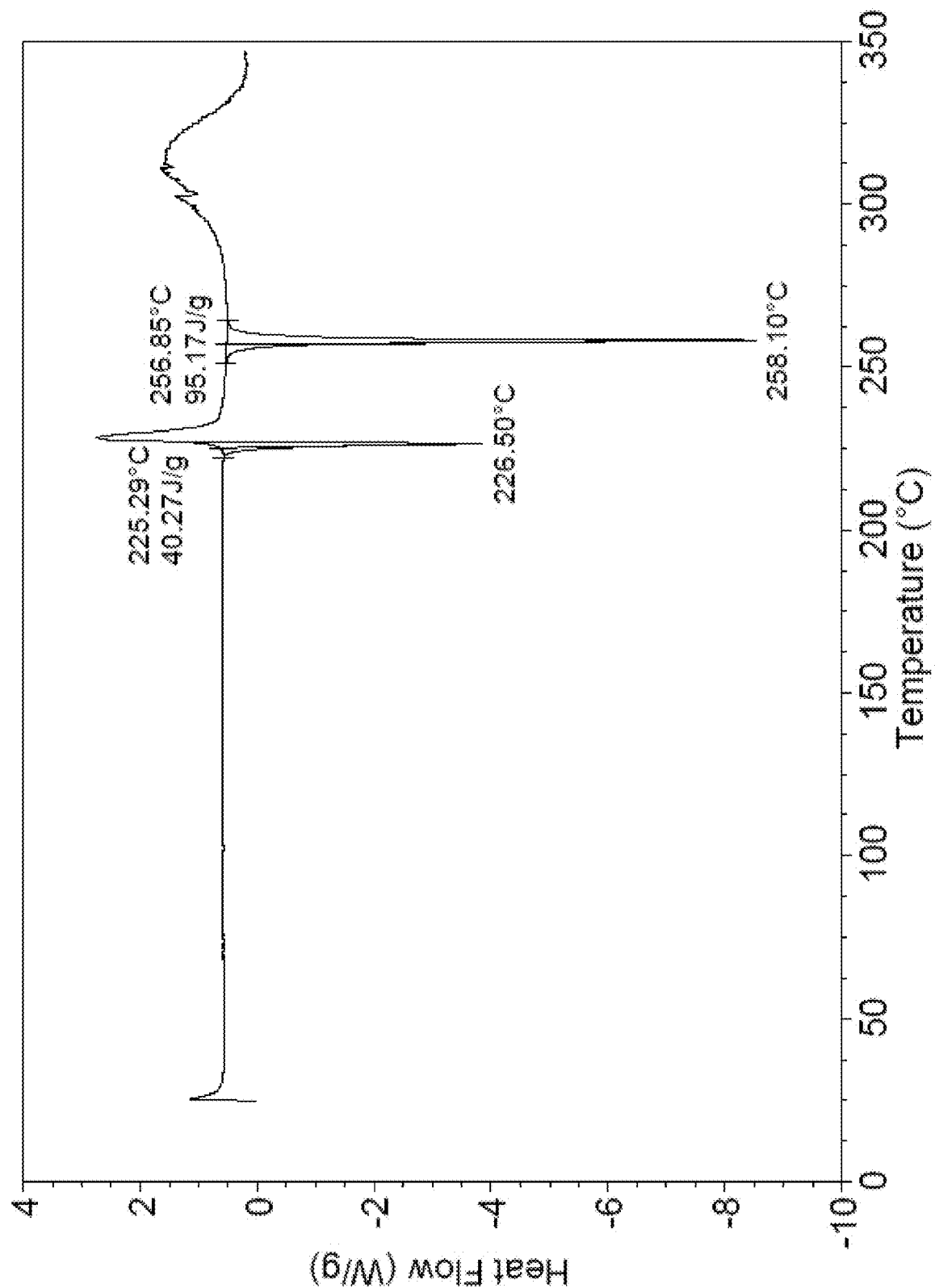
Figure 3:
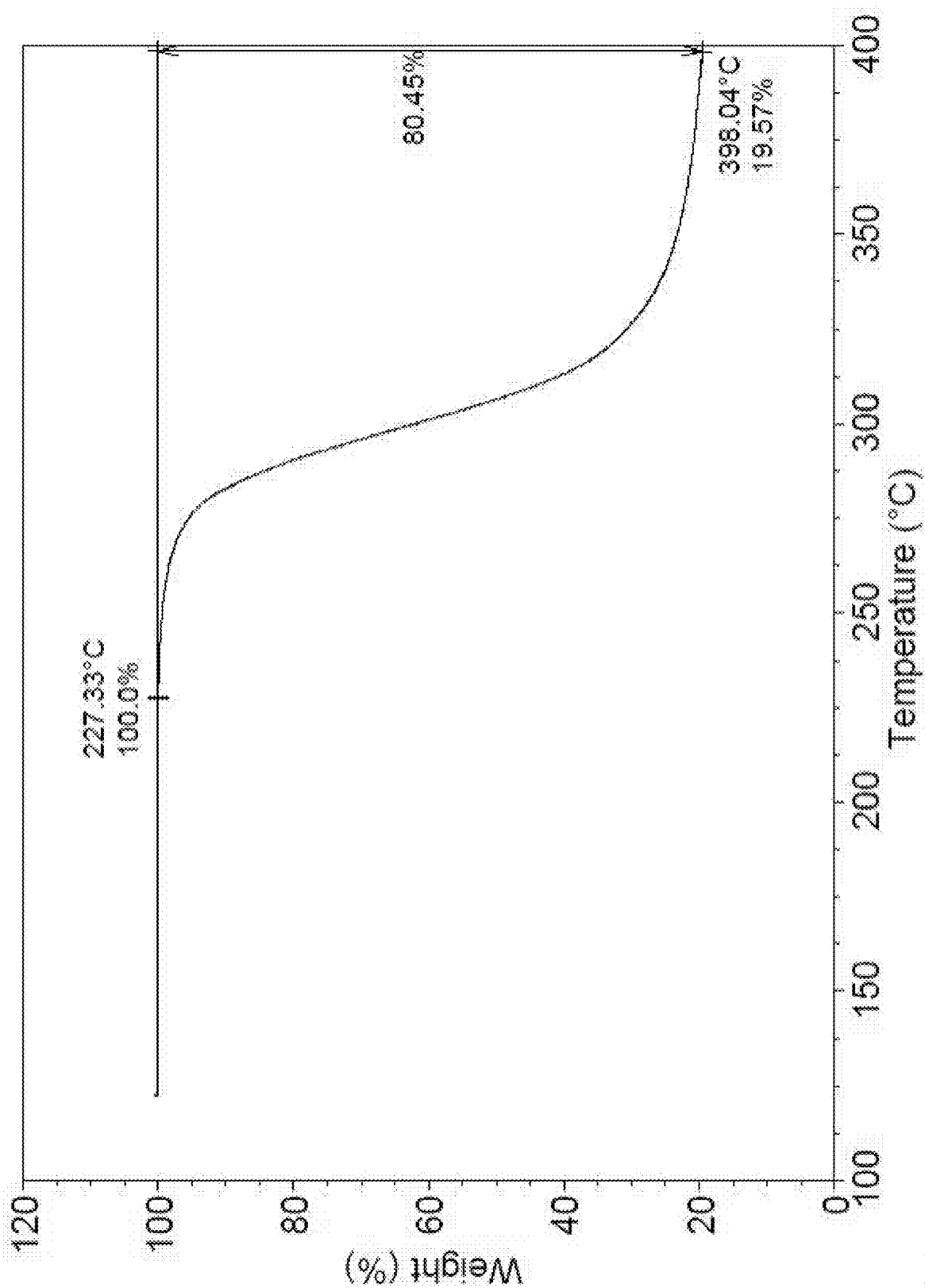

DSC and TGA results shown in FIG. 2 and FIG. 3 indicate Form A of compound (I) has an onset melting temperature at 225.3° C.

Example 2

Preparation of Hydrate Form, Form B of Compound (I)

Figure 4:
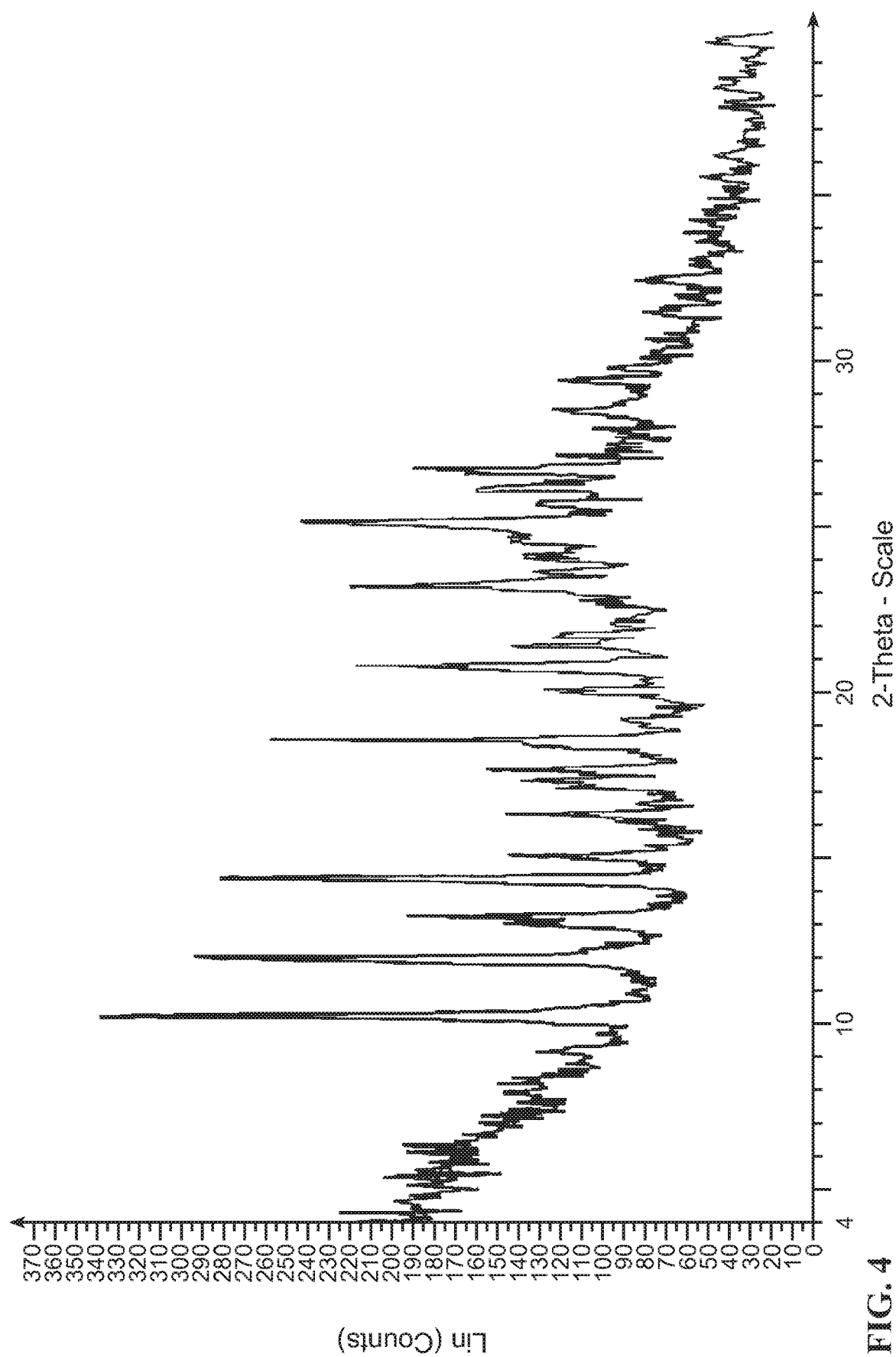

Form B was formed by using Form A as prepared in Example 1 to form a slurry in water at room temperature in 60 hours, then the solid was collected by filtration and dried under vacuum. Form B was characterized by XRPD shown in FIG. 4. Major peaks and their related intensities in the XRPD pattern are shown in Table 2.

Experimental Condition:

XRPD: For crystalline form analysis, sample was mounted in a sample holder on a goniometer and measured at ambient conditions. Data were collected at 2-theta from 4 to 40° with a step size of 0.05° and a scanning speed of is/step on a Bruker D8 Advance X-ray powder diffractometer at 40 KV and 40 mA. Cu-radiation of 1.54 Å wavelength was used for data collection.

DSC analysis: DSC curves were recorded using a TA differential scanning calorimeter Q2000. The sample was heated from 25° C. to 300° C. at a rate of 10° C./min.

TGA analysis: The thermogravimetric analysis was operated on TA Q5000. The sample was heated from 25° C. to 350° C. at a rate of 10° C./min.

TABLE 2

X-Ray Powder Diffraction peaks of Form B of compound (I)

| Pos. [°2 Th.] | Height [cts] | d-spacing [Å] | Rel. Int. [%] |
|---|---|---|---|
| 10.21 | 339 | 8.6608 | 100.0 |
| 11.93 | 294 | 7.4107 | 86.7 |
| 13.22 | 193 | 6.6916 | 56.9 |
| 14.35 | 282 | 6.1670 | 83.2 |
| 15.02 | 145 | 5.8944 | 42.8 |
| 16.31 | 146 | 5.4308 | 43.1 |
| 17.66 | 155 | 5.0181 | 45.7 |
| 18.56 | 258 | 4.7767 | 76.1 |
| 20.06 | 128 | 4.4233 | 37.8 |
| 20.79 | 217 | 4.2687 | 64.0 |
| 21.42 | 143 | 4.1445 | 42.2 |
| 23.24 | 220 | 3.8243 | 64.9 |
| 25.15 | 243 | 3.5386 | 71.7 |
| 26.21 | 160 | 3.3979 | 47.2 |
| 26.74 | 190 | 3.3317 | 56.0 |
| 29.44 | 121 | 3.0316 | 35.7 |

Figure 5:
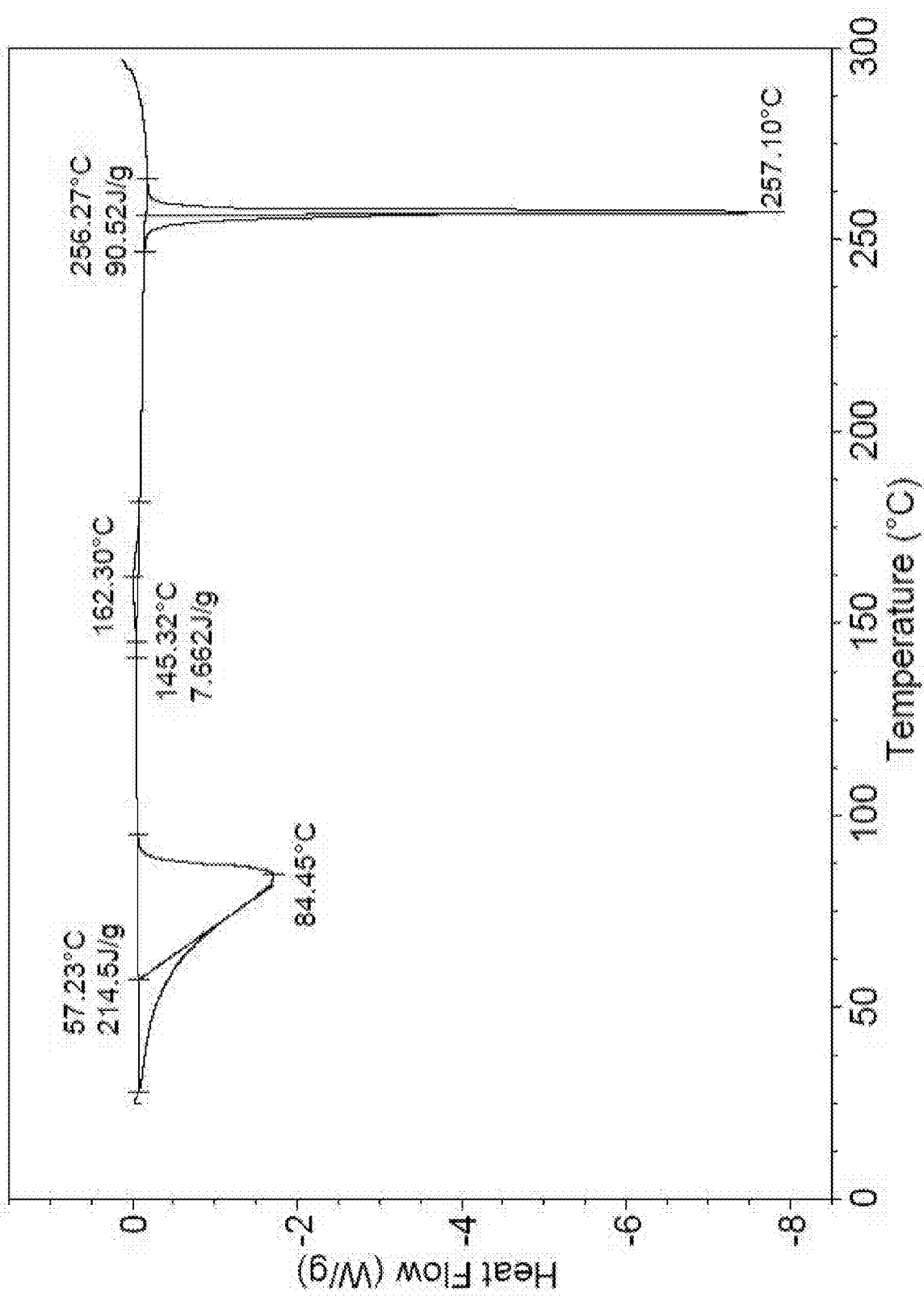
Figure 6:
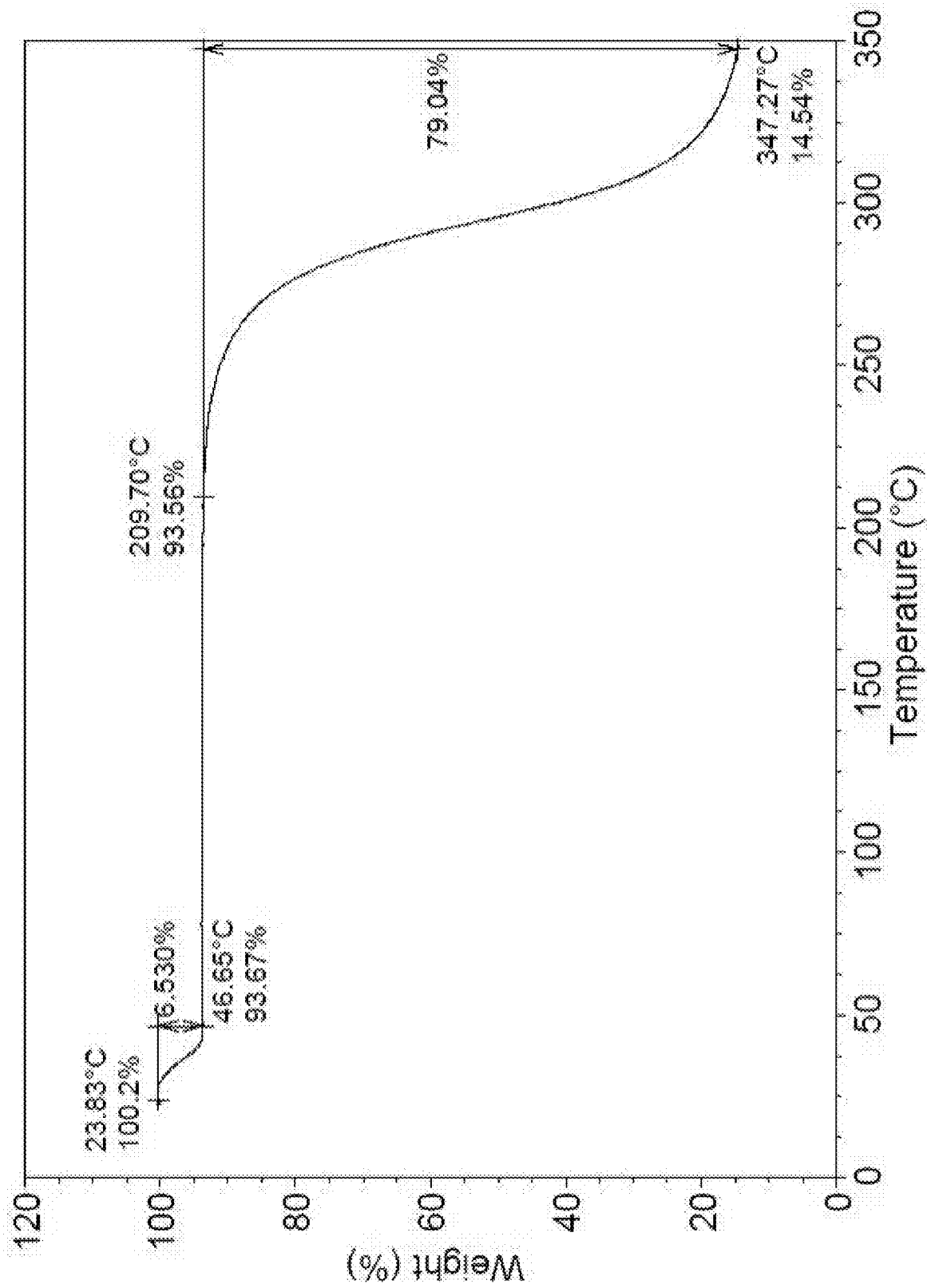

DSC and TGA results shown in FIG. 5 and FIG. 6 indicate Form B of compound (I) has an dehydration temperature at 57.2° C. and onset melting temperature at 256.3° C.

Example 3

Preparation of Form C of Compound (I)

Form A of compound (I) as prepared in Example 1 was heated to 230° C. and kept at 230° C. for 5 minute under vacuum. The solid was obtained as Form C and characterized by)(RFD, DSC and TGA.

Figure 7:
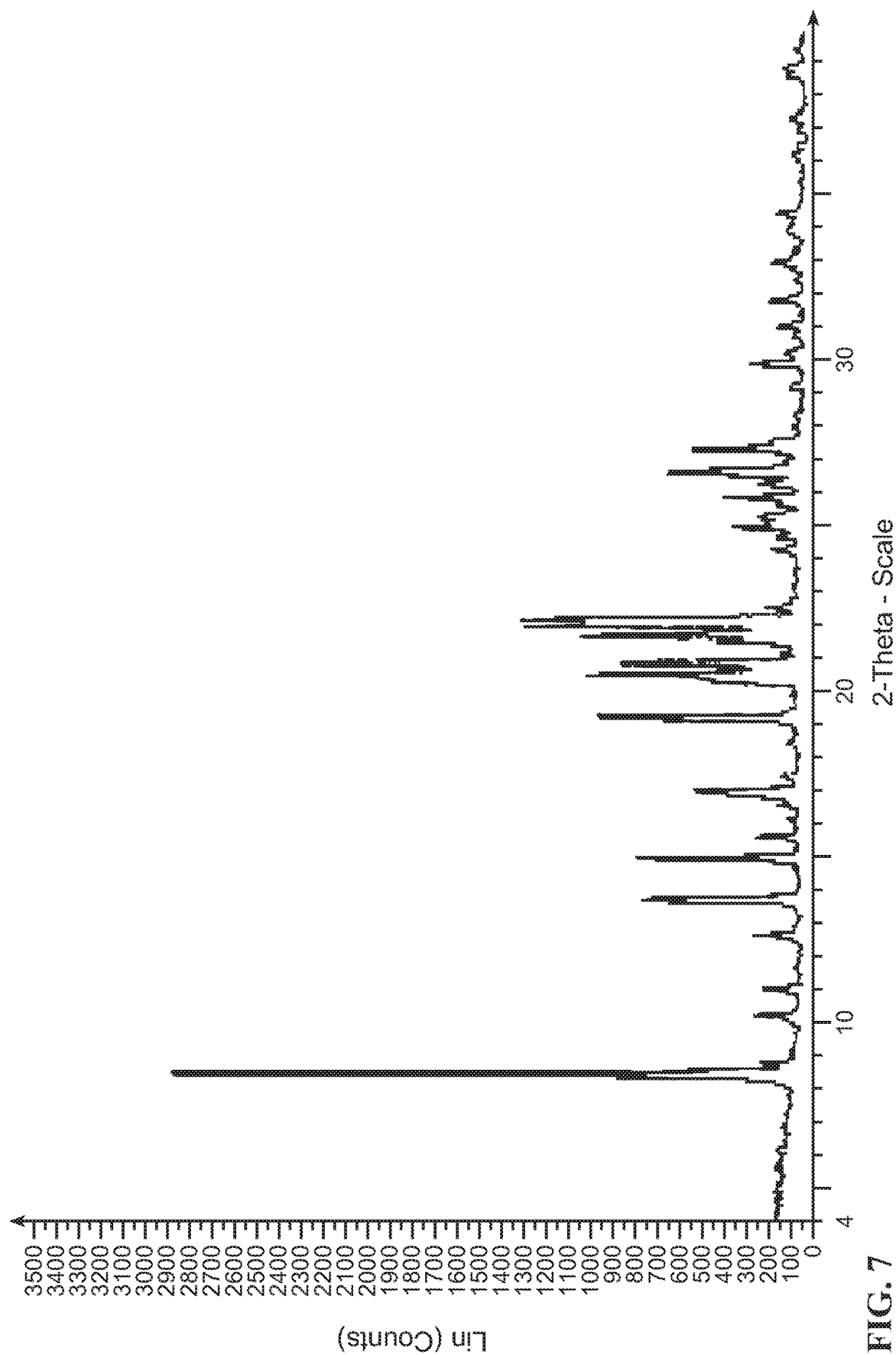

The XRPD pattern of Form C of compound (I) is shown in FIG. 7. Major peaks and their related intensities in the XRPD pattern are shown in Table 3 below.

Experimental Conditions:

XRPD: For crystalline form analysis, sample was mounted in a sample holder on a goniometer and measured at ambient conditions. Data were collected at 2-theta from 4 to 40° with a step size of 0.05° and a scanning speed of is/step on a Bruker D8 Advance X-ray powder diffractometer at 40 KV and 40 mA. Cu-radiation of 1.54 Å wavelength was used for data collection.

DSC analysis: DSC curves were recorded using a TA differential scanning calorimeter Q2000. The sample was heated from 25° C. to 300° C. at a rate of 10° C./min.

TGA analysis: The thermogravimetric analysis was operated on TA Q5000. The sample was heated from 25° C. to 400° C. at a rate of 10° C./min.

TABLE 3

X-Ray Powder Diffraction peaks of Form C of compound (I)

| Pos. [°2 Th.] | Height [cts] | d-spacing [Å] | Rel. Int. [%] |
| --- | --- | --- | --- |
| 8.41 | 2879 | 10.5099 | 100.0 |
| 8.70 | 221 | 10.1579 | 7.7 |
| 10.18 | 258 | 8.6791 | 9.0 |
| 10.98 | 223 | 8.0502 | 7.8 |
| 12.62 | 278 | 7.0088 | 9.7 |
| 13.71 | 755 | 6.4531 | 26.2 |
| 14.95 | 788 | 5.9210 | 27.4 |
| 15.58 | 256 | 5.6830 | 8.9 |
| 16.55 | 160 | 5.3534 | 5.5 |
| 17.01 | 523 | 5.2090 | 18.2 |
| 17.43 | 142 | 5.0844 | 4.9 |
| 19.21 | 954 | 4.6159 | 33.1 |
| 20.49 | 1024 | 4.3302 | 35.6 |
| 20.83 | 858 | 4.2611 | 29.8 |
| 21.46 | 433 | 4.1375 | 15.1 |
| 21.69 | 1031 | 4.0939 | 35.8 |
| 21.99 | 1287 | 4.0398 | 44.7 |
| 22.13 | 1315 | 4.0133 | 45.7 |
| 22.55 | 212 | 3.9395 | 7.4 |
| 24.29 | 186 | 3.6607 | 6.5 |
| 24.67 | 158 | 3.6055 | 5.5 |
| 24.95 | 352 | 3.5667 | 12.2 |
| 25.30 | 245 | 3.5171 | 8.5 |
| 25.85 | 405 | 3.4441 | 14.1 |
| 26.31 | 241 | 3.3847 | 8.4 |
| 26.63 | 648 | 3.3453 | 22.5 |
| 27.34 | 549 | 3.2596 | 19.1 |
| 28.01 | 92 | 3.1829 | 3.2 |
| 29.23 | 103 | 3.0530 | 3.6 |
| 29.92 | 282 | 2.9838 | 9.8 |
| 30.26 | 120 | 2.9515 | 4.2 |
| 30.74 | 83 | 2.9062 | 2.9 |
| 31.04 | 160 | 2.8793 | 5.5 |
| 31.87 | 193 | 2.8053 | 6.7 |
| 32.46 | 81 | 2.7559 | 2.8 |
| 32.78 | 101 | 2.7301 | 3.5 |
| 32.99 | 173 | 2.7132 | 6.0 |
| 33.95 | 114 | 2.6382 | 4.0 |
| 34.46 | 155 | 2.6008 | 5.4 |

Figure 8:
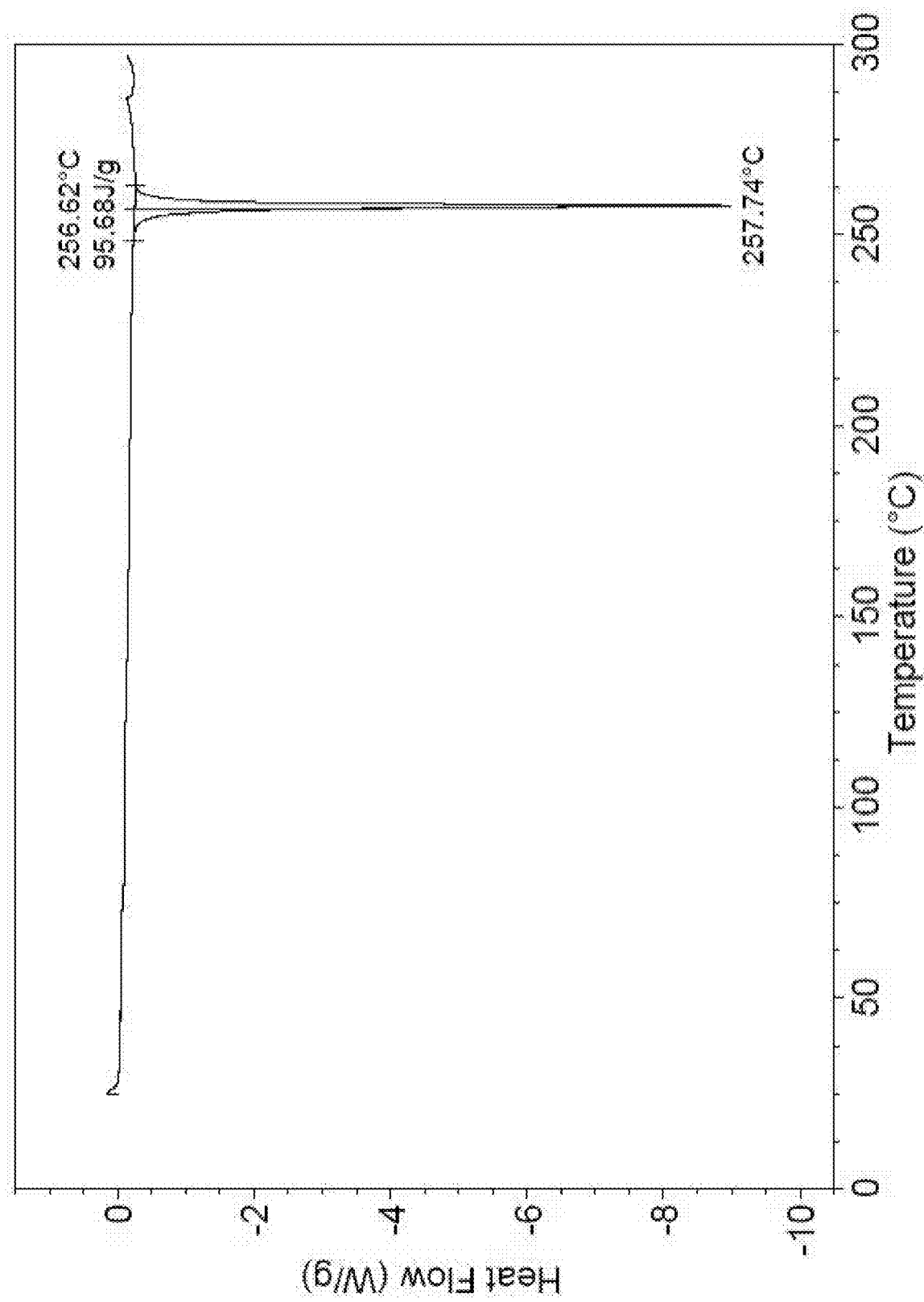
Figure 9:
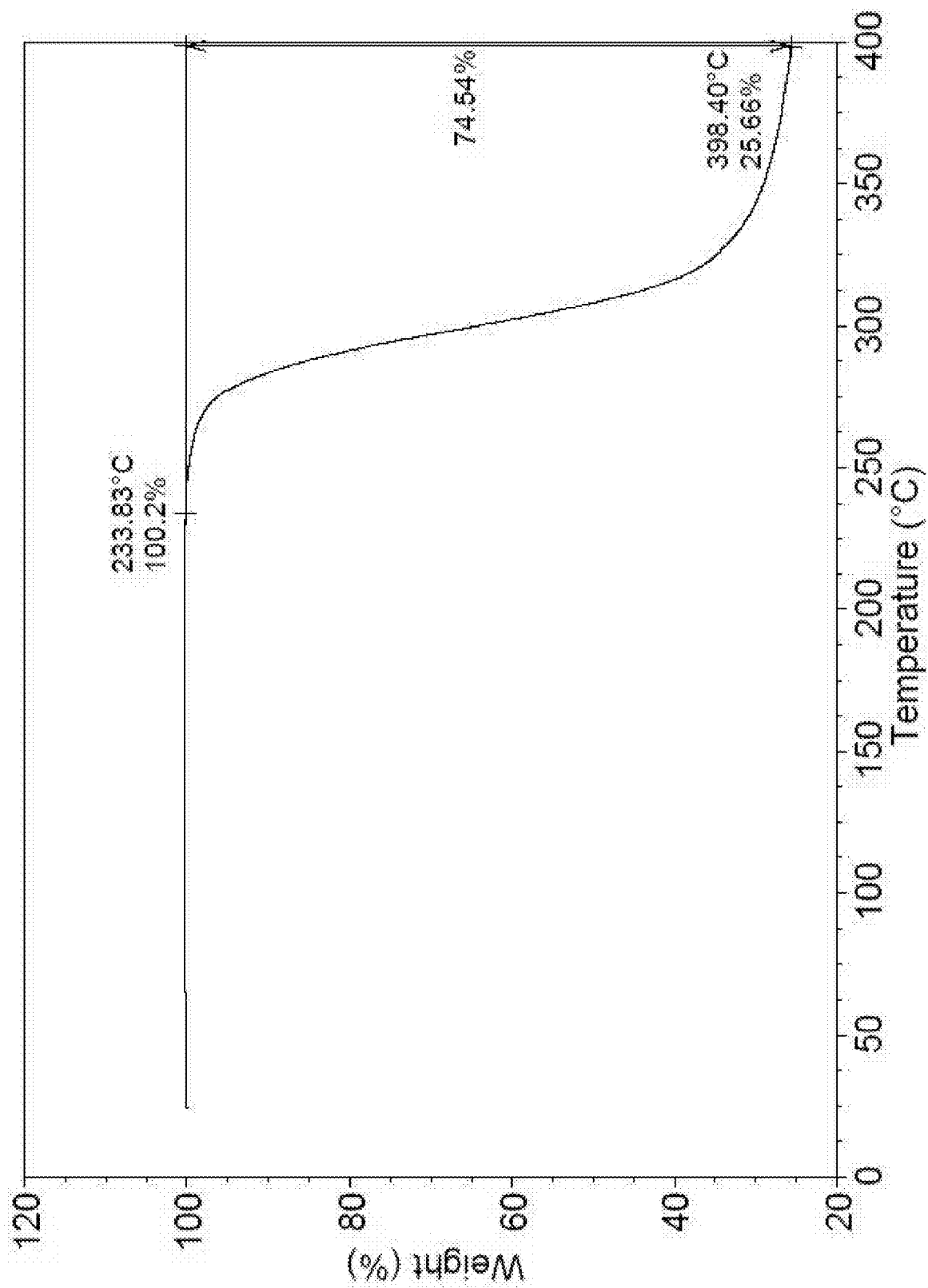

DSC and TGA results shown in FIG. 8 and FIG. 9 indicate Form C of compound (I) has an onset melting temperature at 256.6° C.

Figure 10:
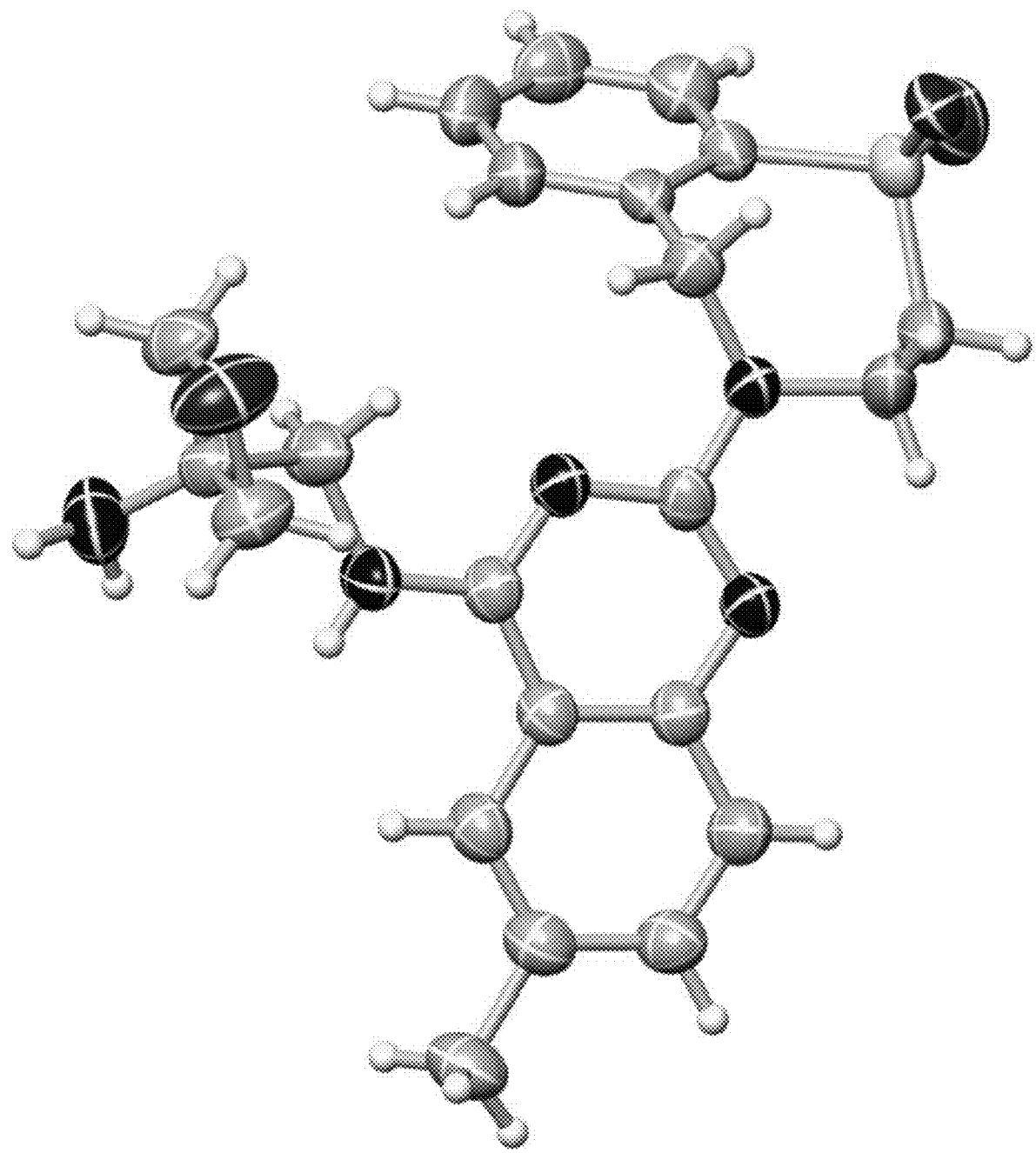

FIG. 10 shows the X-ray structure of Form C of compound (I). The single crystal X-ray intensity data were collected at 293K using a Bruker APEX-II CCD diffractometer (Cu-Kα radiation, λ=1.54178 Å). The crystal data and structure refinement is shown in Table 4.

TABLE 4

Crystal data and structure refinement of Form C of compound (I)

| | |
| --- | --- |
| Empirical formula | $C_{22}H_{25}N_5O_3S$ |
| Formula weight | 439.53 |
| Temperature | 293(2) K |
| Wavelength | 0.70000 Å |
| Crystal system, space group | Triclinic, P-1 |
| Unit cell dimensions | a = 9.2050(18) Å |
| | b = 11.036(2) Å |
| | c = 11.342(2) Å |
| | Alpha = 73.14(3) deg. |
| | Beta = 70.23(3) deg. |
| | Gamma = 87.61(3) deg. |
| Volume | 1035.7(4) Å$^3$ |
| Z, Calculated density | 2, 1.409 mg/mm$^3$ |
| Absorption coefficient | 0.192 mm$^{-1}$ |
| F(000) | 464 |
| Crystal size | 0.2 × 0.10 × 0.02 mm |
| Theta range for data collection | 1.93 to 26.37 deg. |
| Limiting indices | −11 ≤ h ≤ 11 |
| | −13 ≤ k ≤ 13 |
| | −14 ≤ l ≤ 14 |
| Reflections collected/unique | 11747/3795[R(int) = 0.0243] |
| Completeness to theta = 26.37 | 89.3% |
| Absorption correction | None |
| Refinement method | Full matrix least squares on F$^2$ |
| Data/restraints/parameters | 3795/0/294 |
| Goodness-of-fit on F$^2$ | 1.120 |
| Final R indices [I > 2sigma(I)] | R1 = 0.0631 |
| | wR2 = 0.1590 |
| R indices (all data) | R1 = 0.0633 |
| | wR2 = 0.1593 |
| Largest diff peak and hole | 0.514 and −0.584 e · A$^{-3}$ |

Example 4

Preparation of Form D of Compound (I)

Form B of compound (I) as prepared in Example 2 was heated to 60° C. and kept at 60° C. for 2 hours. The solid was obtained as Form D and characterized by XRPD, DSC and TGA.

Figure 11:
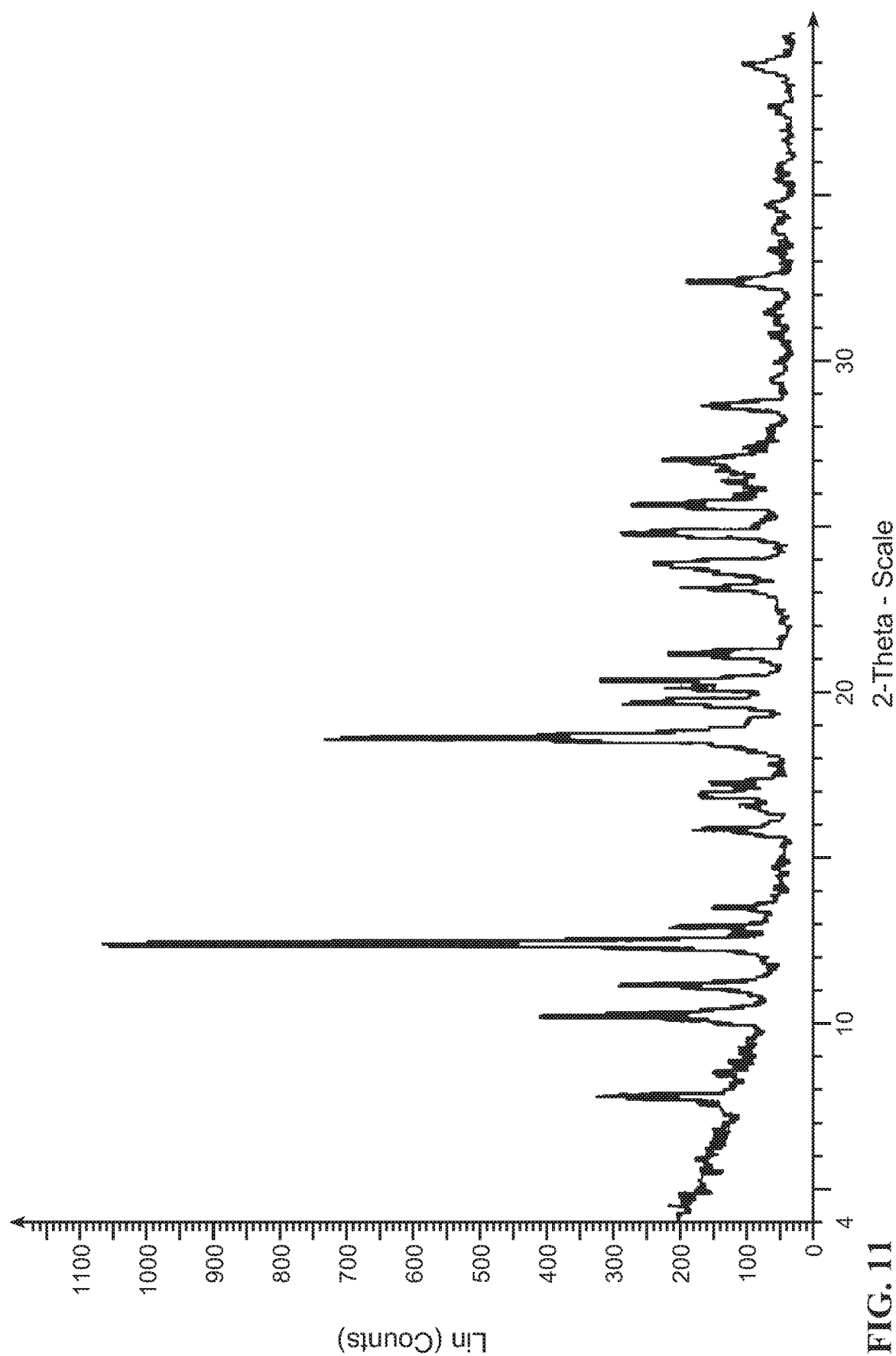

The XRPD pattern of Form D of compound (I) is shown in FIG. 11. Major peaks and their related intensities in the XRPD pattern are shown in Table 5.

Experimental Conditions:

XRPD: For crystalline form analysis, sample was mounted in a sample holder on a goniometer and measured at ambient conditions. Data were collected at 2-theta from 4 to 40° with a step size of 0.05° and a scanning speed of is/step on a Bruker D8 Advance X-ray powder diffractometer at 40 KV and 40 mA. Cu-radiation of 1.54 Å wavelength was used for data collection.

DSC analysis: DSC curves were recorded using a TA differential scanning calorimeter Q2000. The sample was heated from 25° C. to 300° C. at a rate of 10° C./min.

TGA analysis: The thermogravimetric analysis was operated on TA Q5000. The sample was heated from 25° C. to 350° C. at a rate of 10° C./min.

TABLE 5

X-Ray Powder Diffraction peaks of Form D of compound (I)

| Pos. [°2 Th.] | Height [cts] | d-spacing [Å] | Rel. Int. [%] |
|---|---|---|---|
| 7.79 | 312 | 11.3383 | 29.6 |
| 10.18 | 395 | 8.6790 | 37.5 |
| 11.15 | 284 | 7.9313 | 26.9 |
| 12.40 | 1053 | 7.1315 | 100 |
| 12.90 | 200 | 6.8584 | 19 |
| 13.48 | 140 | 6.5627 | 13.3 |
| 15.85 | 170 | 5.5887 | 16.2 |
| 16.57 | 108 | 5.3443 | 10.3 |
| 16.95 | 163 | 5.2256 | 15.5 |
| 17.25 | 152 | 5.1378 | 14.5 |
| 18.68 | 722 | 4.7475 | 68.5 |
| 19.73 | 264 | 4.4970 | 25.1 |
| 20.16 | 211 | 4.4004 | 20 |
| 20.43 | 310 | 4.3444 | 29.5 |
| 21.16 | 209 | 4.1962 | 19.9 |
| 23.14 | 193 | 3.8407 | 18.4 |
| 23.93 | 223 | 3.7160 | 21.2 |
| 24.83 | 278 | 3.5826 | 26.4 |
| 25.71 | 259 | 3.4626 | 24.6 |
| 26.44 | 135 | 3.3687 | 12.8 |
| 27.11 | 213 | 3.2868 | 20.2 |
| 28.68 | 163 | 3.1097 | 15.5 |
| 32.51 | 186 | 2.7522 | 17.7 |
| 39.10 | 94 | 2.3019 | 8.9 |

Figure 12:
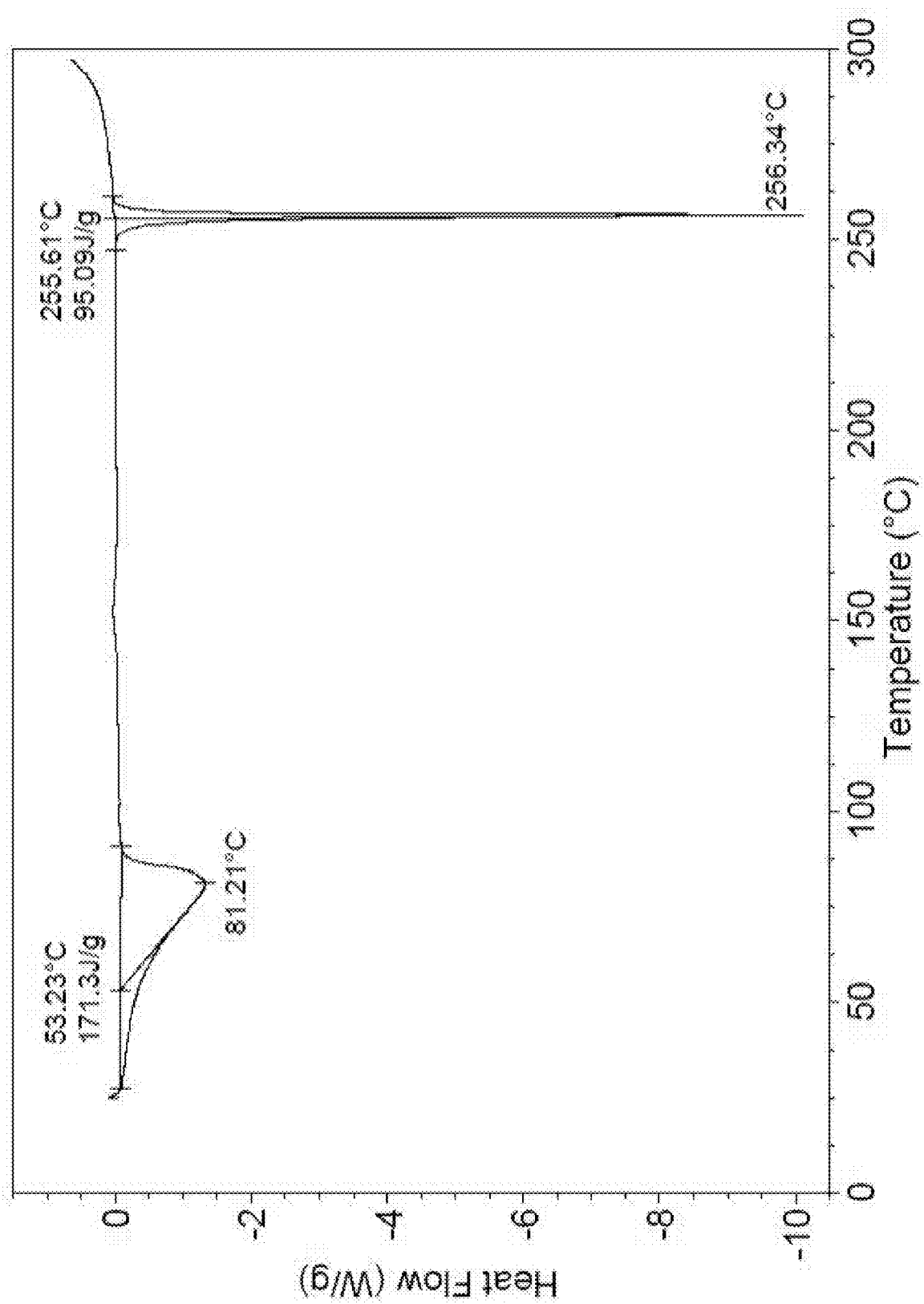
Figure 13:
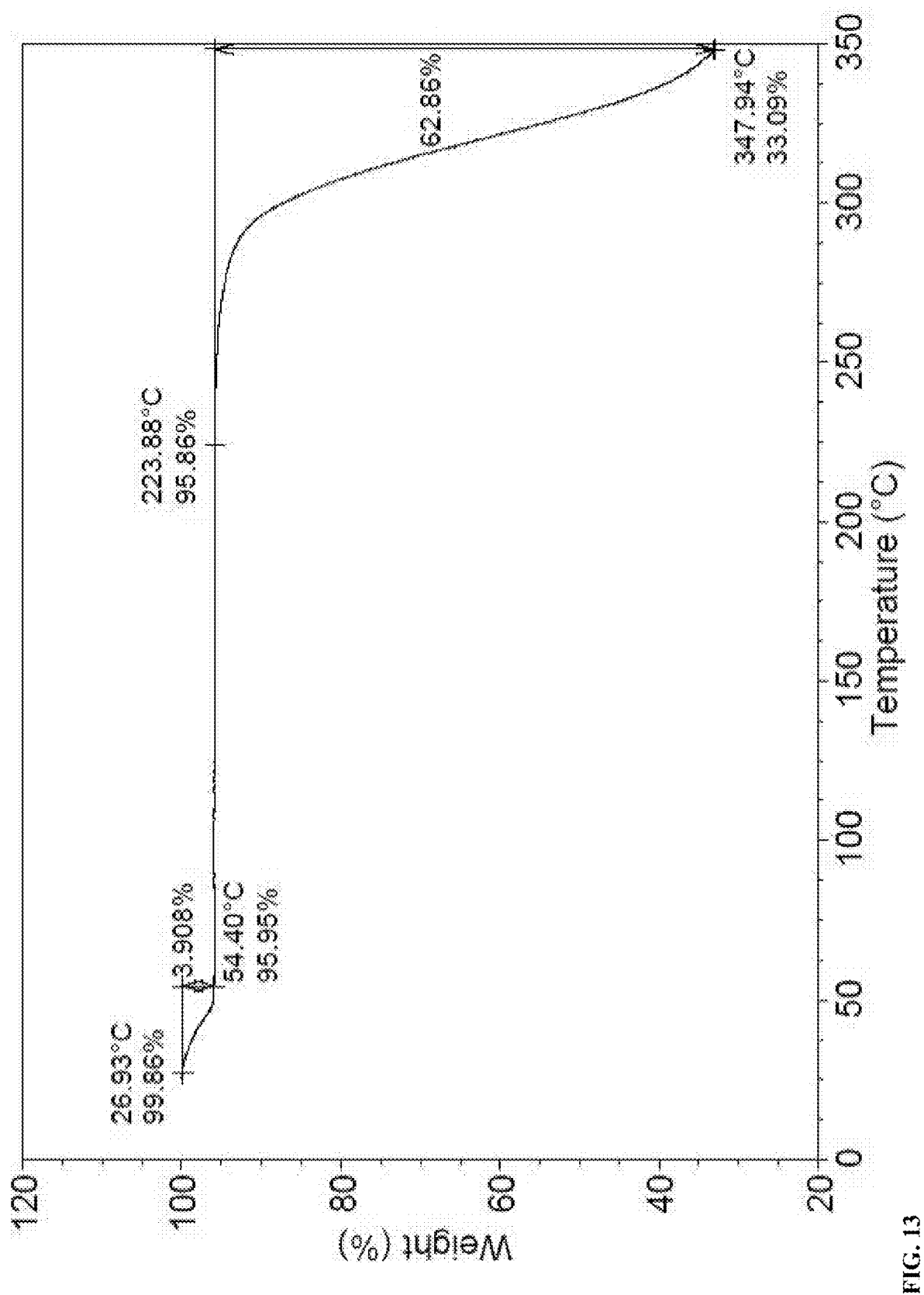

DSC and TGA results shown in FIG. 12 and FIG. 13 indicate Form D of compound (I) has an dehydration temperature at 53.2° C. and onset melting temperature at 255.6° C.

Example 5

Preparation of Mono Acetate Salt Form E of Compound (I)

44 mg of Form C of compound (I) as prepared in Example 3 was dissolved in 440 μL ethyl acetate. Equal molar acetic acid was added to previous reaction mixture. The mixture was stirred at room temperature overnight to generate precipitation. The solid was isolated as Form E for XRPD analysis.

Figure 14:
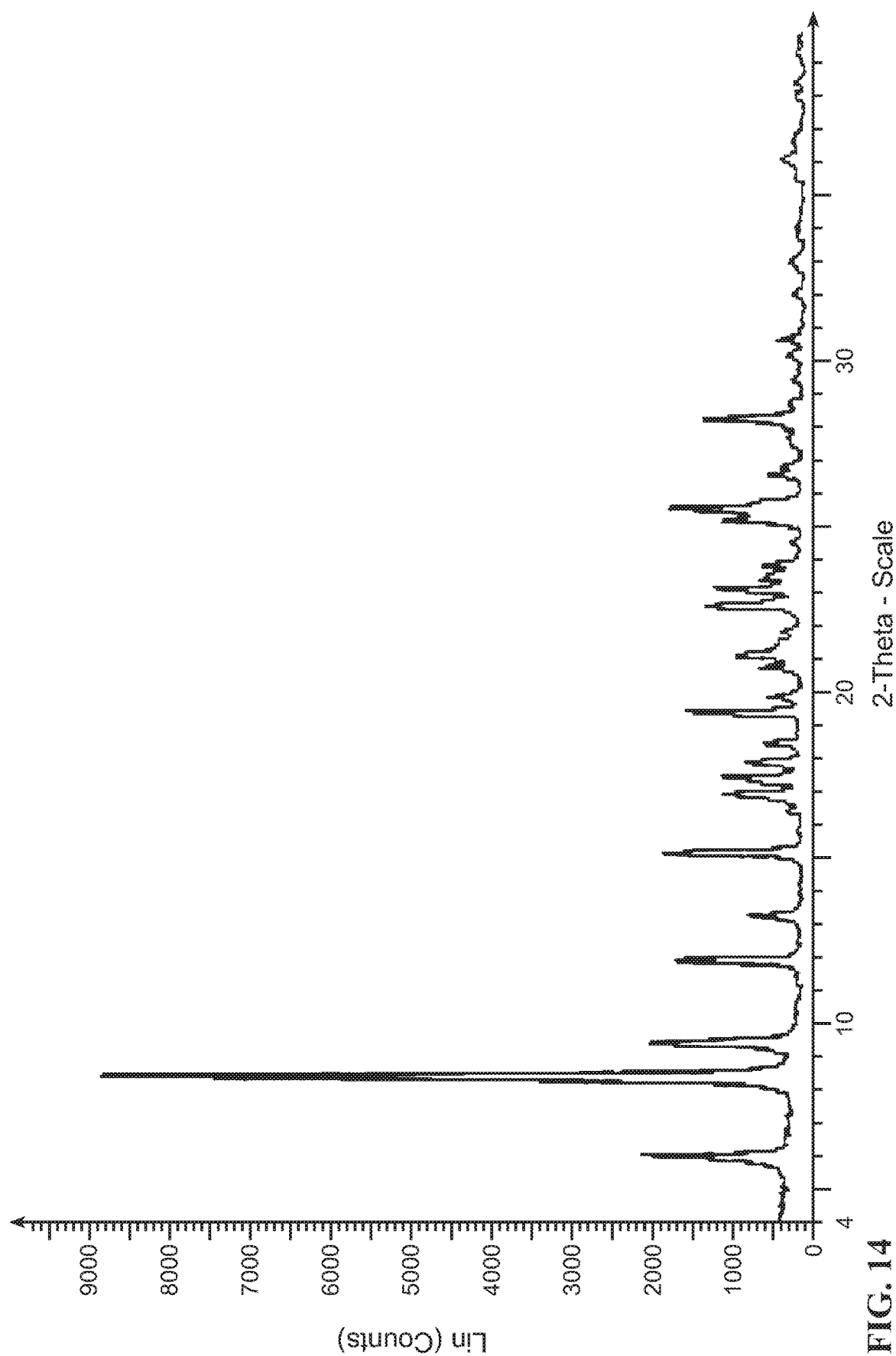

The XRPD pattern of mono acetate salt Form E of compound (I) is shown in FIG. 14. Major peaks and their related intensities in the XRPD pattern are shown in Table 6.

Experimental Conditions:

XRPD: For crystalline form analysis, sample was mounted in a sample holder on a goniometer and measured at ambient conditions. Data were collected at 2-theta from 4 to 40° with a step size of 0.05° and a scanning speed of is/step on a Bruker D8 Advance X-ray powder diffractometer at 40 KV and 40 mA. Cu-radiation of 1.54 Å wavelength was used for data collection.

TABLE 6

X-Ray Powder Diffraction peaks of mono acetate salt Form E of compound (I)

| Pos. [°2 Th.] | Height [cts] | d-spacing [Å] | Rel. Int. [%] |
|---|---|---|---|
| 5.96 | 2044 | 14.82996 | 23.1 |
| 8.32 | 8852 | 10.61968 | 100.0 |
| 9.34 | 1956 | 9.4603 | 22.1 |
| 11.82 | 1647 | 7.4798 | 18.6 |
| 13.22 | 750 | 6.6902 | 8.5 |
| 15.09 | 1691 | 5.8660 | 19.1 |
| 16.90 | 1088 | 5.2417 | 12.3 |
| 17.46 | 1103 | 5.0764 | 12.5 |
| 17.81 | 721 | 4.9773 | 8.1 |
| 18.42 | 529 | 4.8130 | 6.0 |
| 19.44 | 1485 | 4.5623 | 16.8 |
| 19.88 | 471 | 4.4628 | 5.3 |
| 20.78 | 676 | 4.2705 | 7.6 |
| 21.08 | 956 | 4.2120 | 10.8 |
| 22.59 | 1323 | 3.9323 | 15.0 |
| 23.12 | 1162 | 3.8441 | 13.1 |
| 23.53 | 573 | 3.7783 | 6.5 |
| 23.88 | 603 | 3.7237 | 6.8 |
| 25.25 | 1088 | 3.5244 | 12.3 |
| 25.60 | 1706 | 3.4769 | 19.3 |
| 26.65 | 515 | 3.3422 | 5.8 |
| 28.34 | 1250 | 3.1463 | 14.1 |
| 30.74 | 382 | 2.9065 | 4.3 |

Example 6

Preparation of Mono Maleic Salt Form F of Compound (I)

44 mg of Form C of compound (I) as prepared in Example 3 was dissolved in 440 μL ethanol. Equal molar maleic acid was added to previous reaction mixture. The mixture was stirred at room temperature overnight to generate precipitation. The solid was isolated as Form F for XRPD analysis.

Figure 15:
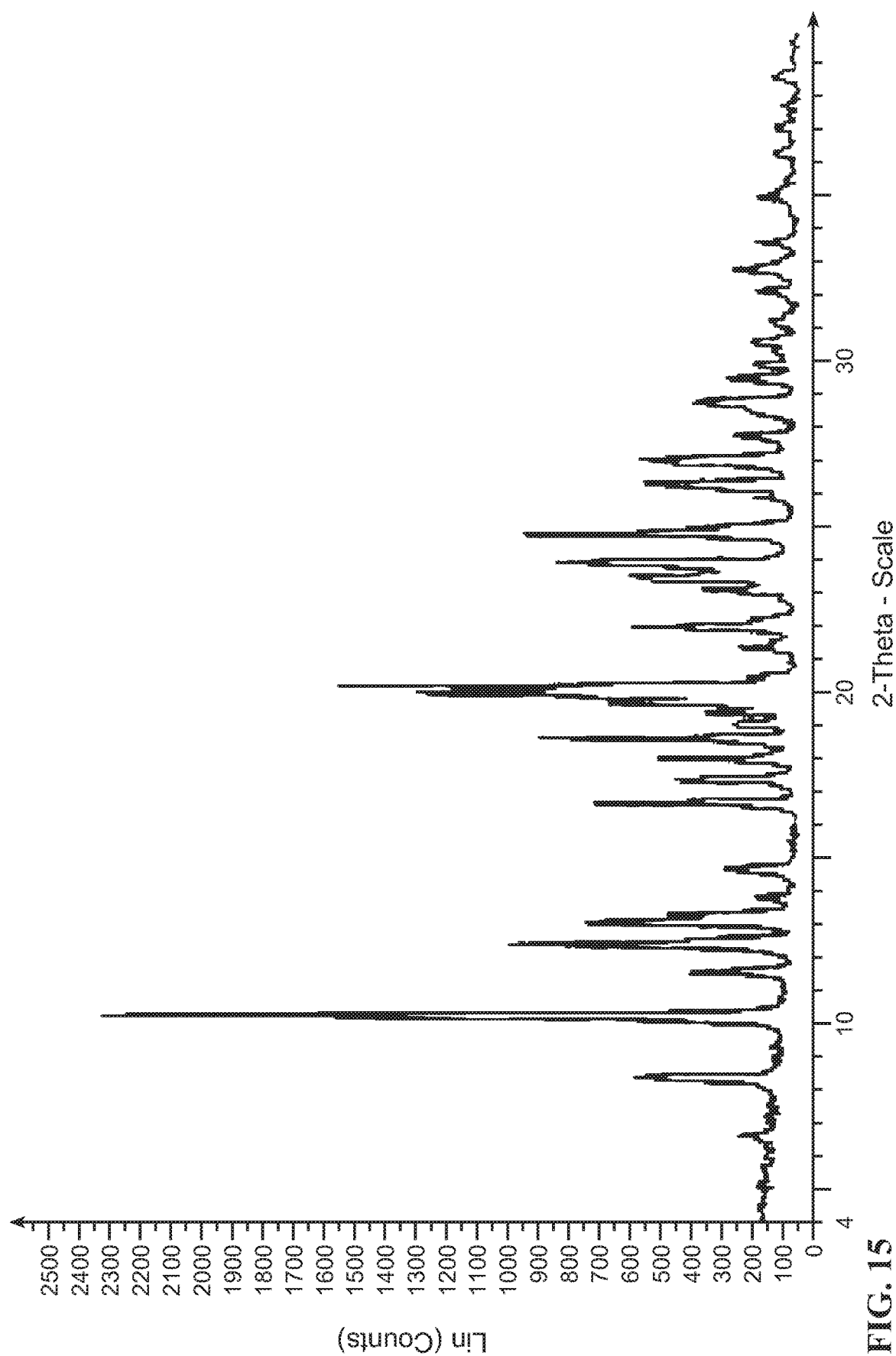

The XRPD pattern of mono maleic salt Form F of compound (I) is shown in FIG. 15. Major peaks and their related intensities in the XRPD pattern are shown in Table 7.

Experimental Conditions:

XRPD: For crystalline form analysis, sample was mounted in a sample holder on a goniometer and measured at ambient conditions. Data were collected at 2-theta from 4 to 40° with a step size of 0.05° and a scanning speed of is/step on a Bruker D8 Advance X-ray powder diffractometer at 40 KV and 40 mA. Cu-radiation of 1.54 Å wavelength was used for data collection.

TABLE 7

X-Ray Powder Diffraction peaks of mono maleic salt Form F of compound (I)

| Pos. [°2 Th.] | Height [cts] | d-spacing [Å] | Rel. Int. [%] |
|---|---|---|---|
| 8.32 | 515 | 10.6204 | 22.1 |
| 10.27 | 2329 | 8.6028 | 100.0 |
| 11.53 | 379 | 7.6690 | 16.3 |
| 12.38 | 983 | 7.1463 | 42.2 |
| 13.05 | 735 | 6.7801 | 31.6 |
| 13.78 | 170 | 6.4226 | 7.3 |
| 14.62 | 286 | 6.0526 | 12.3 |
| 16.58 | 696 | 5.3428 | 29.9 |
| 17.31 | 441 | 5.1192 | 18.9 |
| 18.01 | 484 | 4.9216 | 20.8 |
| 18.59 | 836 | 4.7684 | 35.9 |
| 19.00 | 267 | 4.6667 | 11.5 |
| 19.32 | 341 | 4.5899 | 14.6 |
| 19.70 | 619 | 4.5024 | 26.6 |
| 19.91 | 1250 | 4.4566 | 53.7 |
| 20.14 | 1412 | 4.4055 | 60.6 |
| 21.28 | 224 | 4.1723 | 9.6 |
| 22.01 | 580 | 4.0356 | 24.9 |
| 23.15 | 333 | 3.8396 | 14.3 |
| 23.56 | 588 | 3.7739 | 25.2 |
| 23.93 | 836 | 3.7149 | 35.9 |
| 24.78 | 921 | 3.5899 | 39.5 |
| 26.39 | 499 | 3.3750 | 21.4 |

TABLE 7-continued

X-Ray Powder Diffraction peaks of mono maleic salt Form F of compound (I)

| Pos. [°2 Th.] | Height [cts] | d-spacing [Å] | Rel. Int. [%] |
|---|---|---|---|
| 27.09 | 480 | 3.2893 | 20.6 |
| 27.76 | 248 | 3.2113 | 10.6 |
| 28.84 | 364 | 3.0934 | 15.6 |
| 29.54 | 279 | 3.0216 | 12.0 |
| 29.92 | 174 | 2.9842 | 7.5 |
| 30.53 | 201 | 2.9256 | 8.6 |
| 32.17 | 186 | 2.7806 | 8.0 |
| 32.81 | 221 | 2.7276 | 9.5 |
| 33.63 | 163 | 2.6632 | 7.0 |
| 34.94 | 190 | 2.5660 | 8.1 |

Example 7

Hygroscopicity of Crystal Forms

Dynamic vapour sorption (DVS) was tested using a DVS intrinsic from SMS (Surface Measurement Systems Co. Ltd.). 20 mg compound (I) of each crystal form was placed in an aluminium sample pan and recorded the sample weight change under different humidity. The DVS method parameters were set according to Table 16, and the method was run by the machine based on such parameters.

The hygroscopicity results of different crystal forms are shown in Table 17. According to the hygroscopicity results, the Form A, C, E and F of compound (I) showed much improved hygroscopicity than Form D.

TABLE 16

The testing parameters of DVS

| Parameters | Value |
|---|---|
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH-95% RH-0% RH |
| RH step size | 5% (0% RH-95% RH-0% RH) |

TABLE 17

The results of hygroscopicity test.

Figure 16:
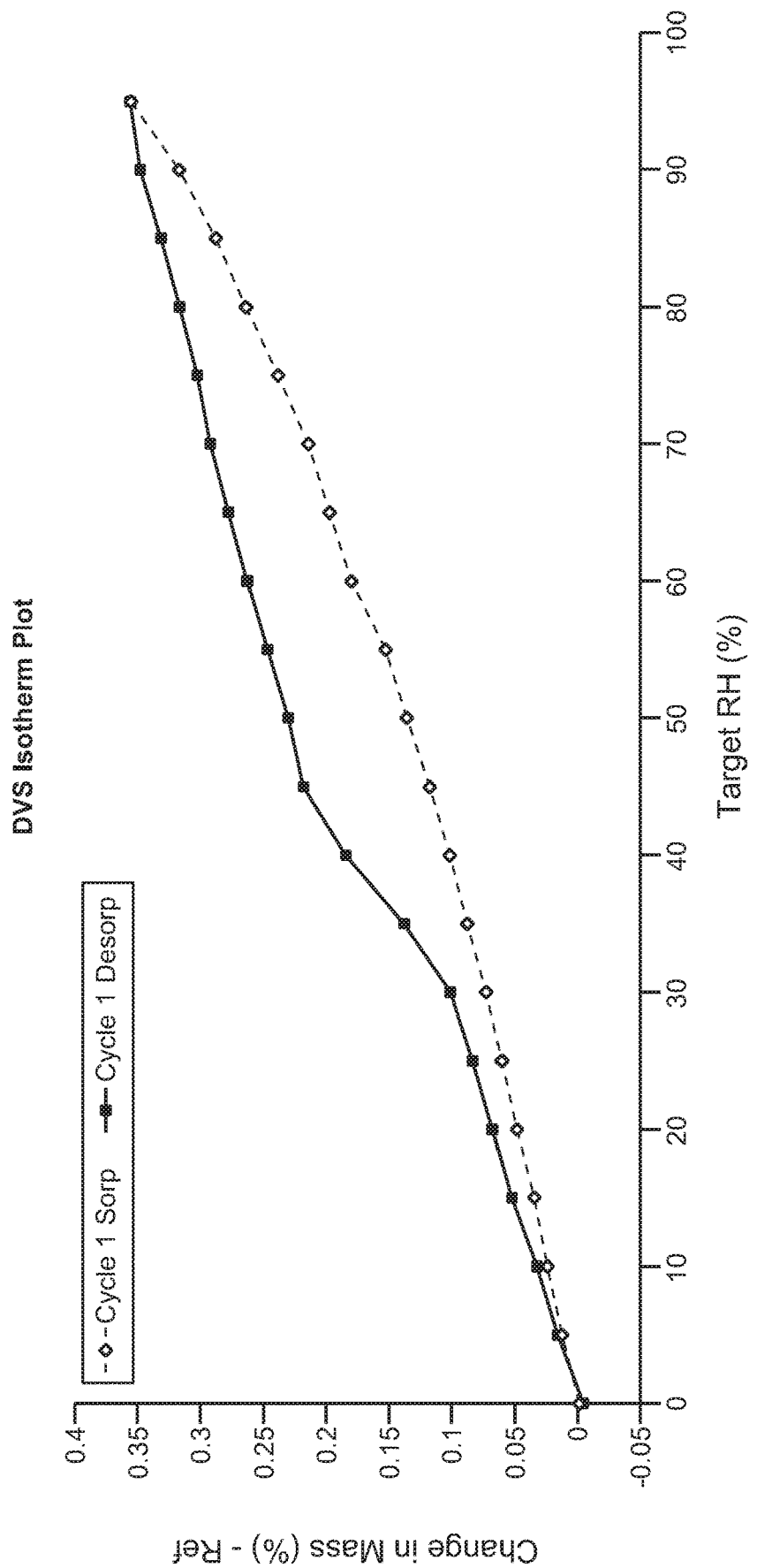
Figure 17:
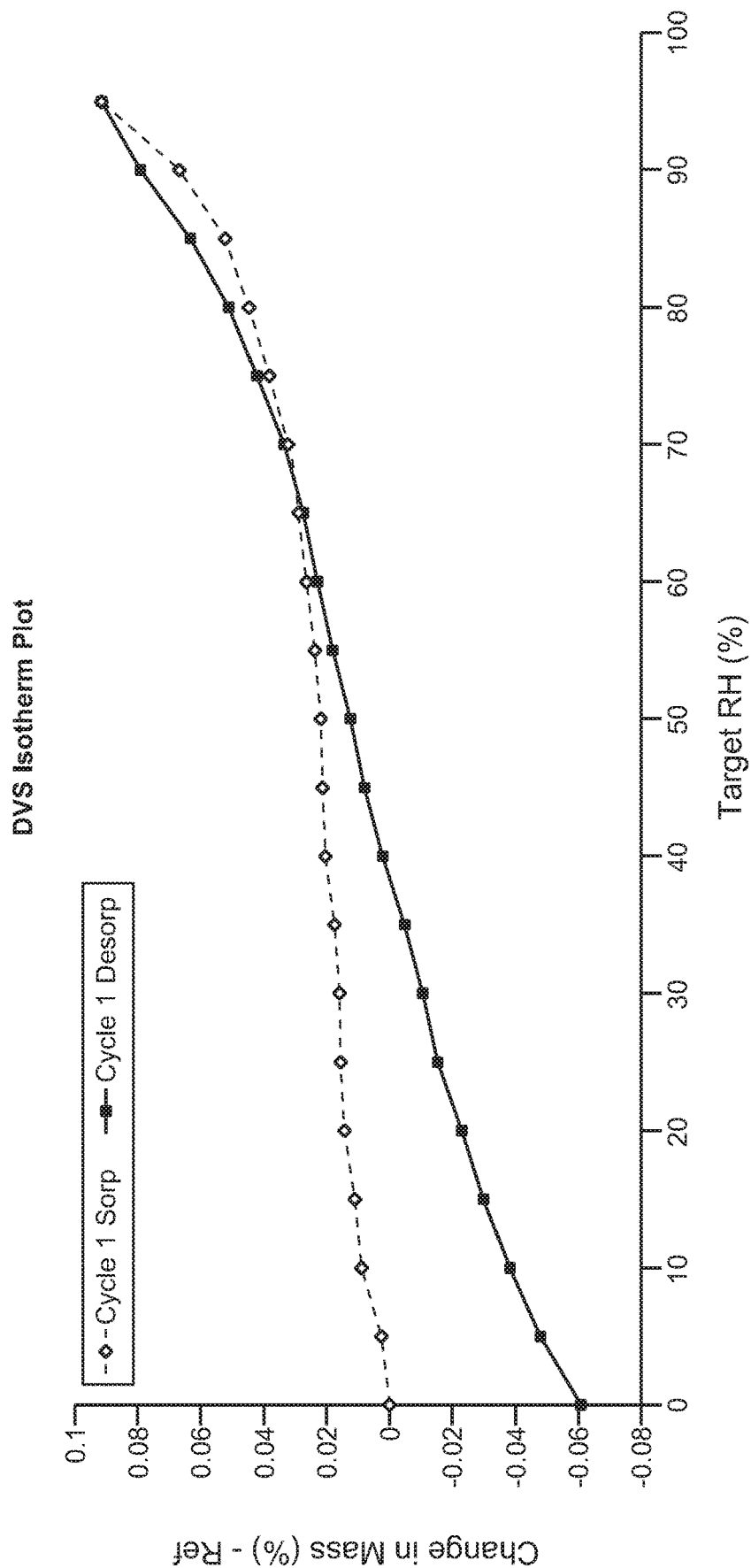

| Samples | Hygroscopicity | FIG. No. |
|---|---|---|
| Example 1, Form A of compound (I) | 0.25% water sorption @80% RH | FIG. 16 |
| Example 3, Form C of compound (I) | 0.04% water sorption @80% RH | FIG. 17 |

TABLE 17-continued

The results of hygroscopicity test.

Figure 18:
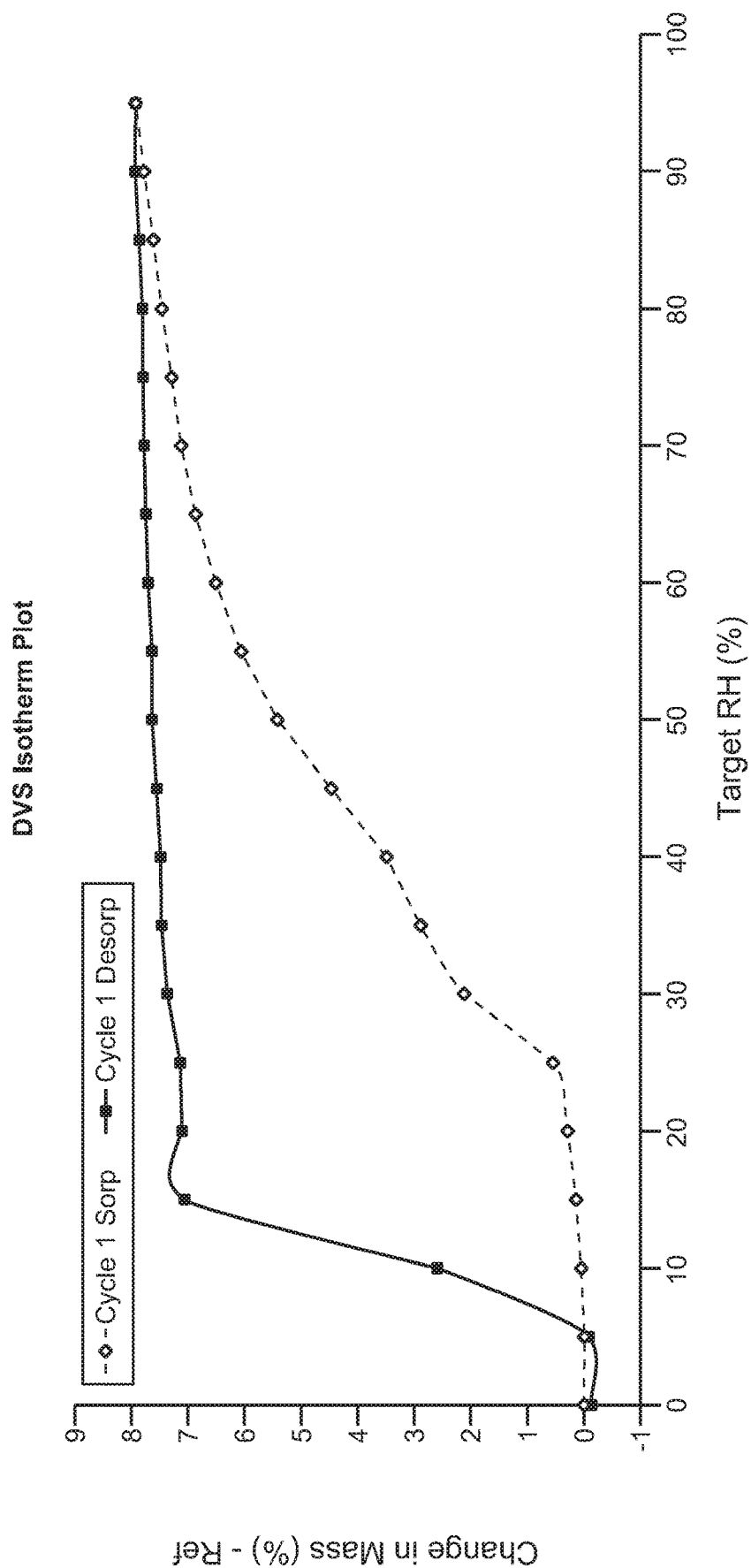
Figure 19:
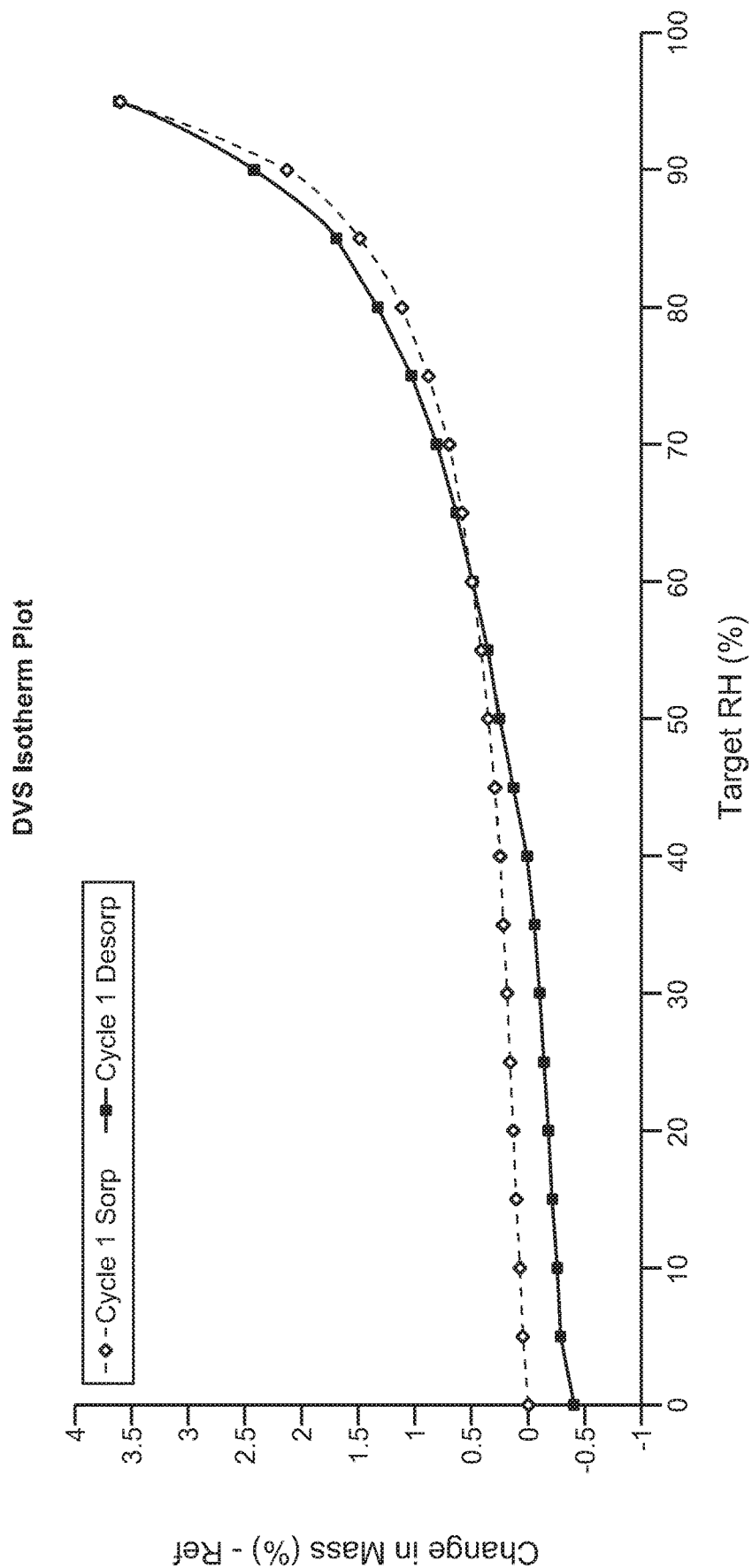
Figure 20:
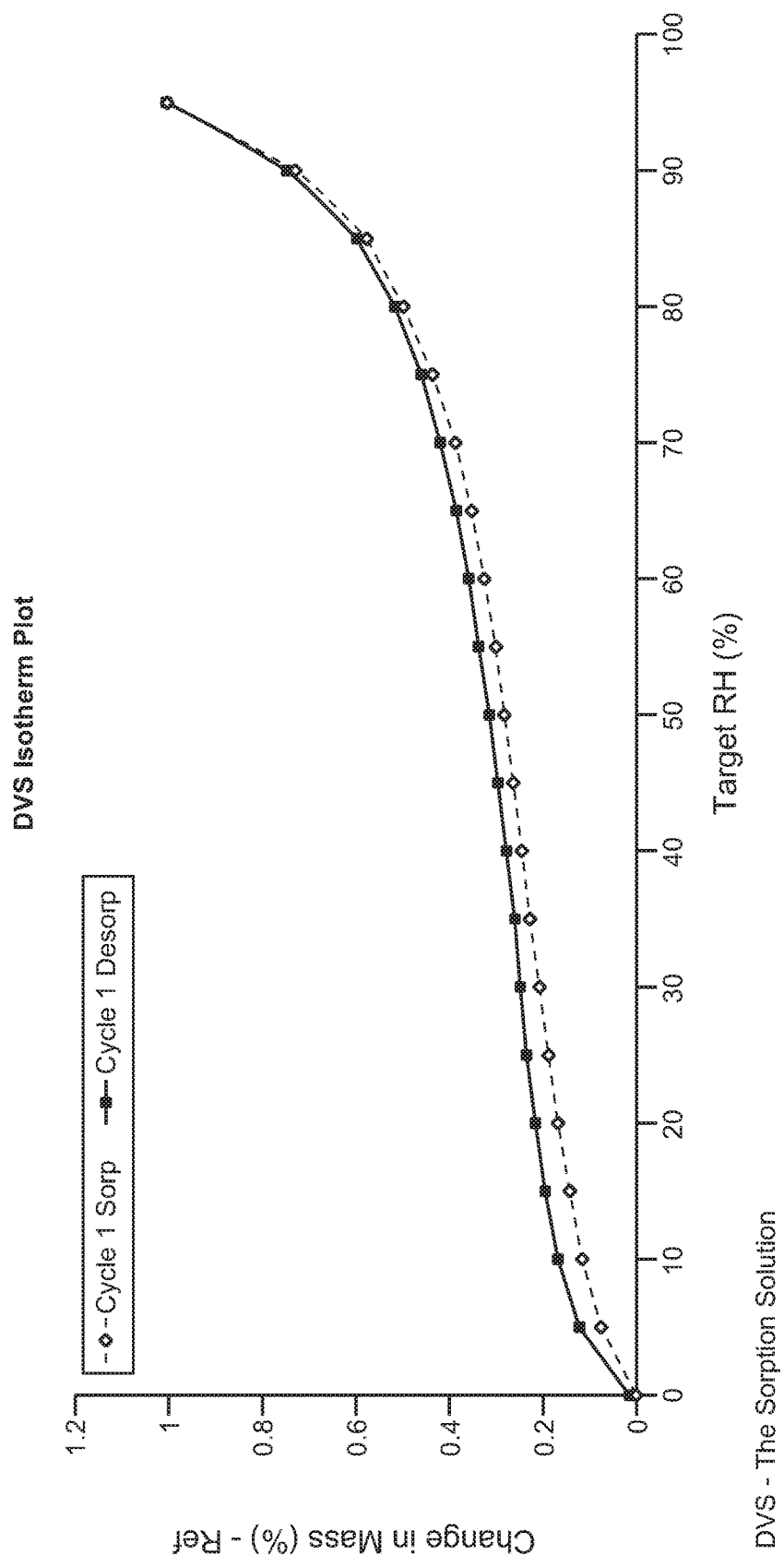

| Samples | Hygroscopicity | FIG. No. |
|---|---|---|
| Example 4, Form D of compound (I) | 7.52% water sorption @80% RH | FIG. 18 |
| Example 5, Form E of compound (I) | 1.12% water sorption @80% RH | FIG. 19 |
| Example 6, Form F of compound (I) | 0.50% water sorption @80% RH | FIG. 20 |

Example 8

Chemical Stability of Crystal Forms 40 mg compound (I) of crystal Forms C, E and F were stored in stability chamber with temperature and humidity controlled as 50° C. and 40° C./75% RH respectively, 40 mg compound (I) of Form B was stored at 105° C. oven. After each time point, the samples were analyzed by HPLC to check their chemical purity and compared with their initial value. According to the results shown in Table 18, all crystal forms of compound (I) showed good chemical stability properties.

TABLE 18

Chemical stability data of different crystal forms of compound (I)

| Samples | Conditions | Time point | Chemical Purity, % |
|---|---|---|---|
| Example 2, Form B of compound (I) | — | Initial | 99.81% |
|  | 105° C. | 24 hr | 99.80% |
| Example 3, Form C of compound (I) | — | Initial | 99.30% |
|  | 50° C. | 1 month | 99.32% |
|  | 40° C./75% RH |  | 99.28% |
| Example 5, Form E of compound (I) | — | Initial | 99.49% |
|  | 50° C. | 1 month | 99.45% |
|  | 40° C./75% RH |  | 99.14% |
| Example 6, Form F of compound (I) | — | Initial | 99.62% |
|  | 50° C. | 1 month | 99.43% |
|  | 40° C./75% RH |  | 99.42% |

Example 9

Equilibrium Aqueous Solubility

Aqueous solubility was determined by suspending 10 mg compound in different bio-relevant media including SGF, FaSSIF and FeSSIF. The suspension was equilibrated at 25° C. for 24 hours then the final pH was measured. The suspension was then filtered through a 0.22 um PVDF filter into a 2-mL HPLC vial. The quantitation was conducted by HPLC (described in Example 10) with reference to a standard solution. The solubility results of selected novel crystal forms in this invention are shown in Table 19 which showed good aqueous solubility higher than 0.1 mg/mL.

TABLE 19

Aqueous solubility of different crystal forms

| | SGF | | FaSSIF | | FeSSIF | |
|---|---|---|---|---|---|---|
| Samples | S, mg/mL | Final pH | S, mg/mL | Final pH | S, mg/mL | Final pH |
| Example 1, Form A of compound (I) | 2.40 | 4.80 | 0.12 | 6.60 | 1.72 | 5.31 |
| Example 3, Form C of compound (I) | 3.81 | 4.92 | 0.11 | 6.63 | 1.88 | 5.26 |

TABLE 19-continued

| | Aqueous solubility of different crystal forms | | | | | |
|---|---|---|---|---|---|---|
| | SGF | | FaSSIF | | FeSSIF | |
| Samples | S, mg/mL | Final pH | S, mg/mL | Final pH | S, mg/mL | Final pH |
| Example 5, Form E of compound (I) | >5 | 4.69 | 0.90 | 5.31 | 2.18 | 5.34 |
| Example 6, Form F of compound (I) | >5 | 3.15 | 1.58 | 4.99 | 1.99 | 5.18 |

The invention claimed is:

1. A method for the treatment or prophylaxis of respiratory syncytial virus infection or a disease caused by respiratory syncytial virus infection, which method comprises administering a therapeutically effective amount of the crystalline form of the compound of formula (I):

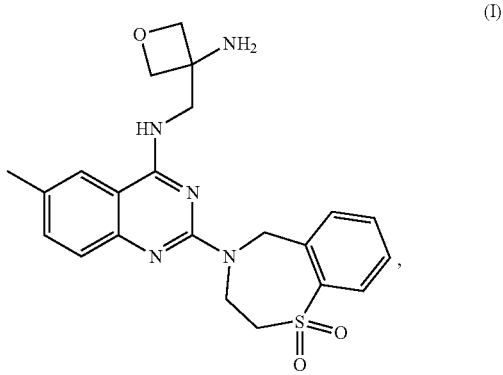 [SMILES: Cc1ccc2nc(N3CCS(=O)(=O)c4ccccc4C3)nc(NCC3(N)COC3)c2c1]

(I)

or a salt, solvent or combination of salts and solvates thereof; wherein the crystalline form is Form A, Form B, Form C, Form D, Form E or Form F, or a combination thereof.

2. The method of claim 1, wherein the crystalline form is Form A that exhibits an X-ray powder diffraction (XRPD) pattern with characteristic peaks expressed in degrees 2-theta at 9.79°±0.10°, 10.64°±0.10°, 16.79°±0.10°, 17.51°±0.10°, 20.12°±0.10°, 21.62°±0.10° and 25.79°±0.10°.

3. The method of claim 2, wherein the crystalline form is Form A that exhibits an X-ray powder diffraction (XRPD) pattern with characteristic peaks expressed in degrees 2-theta at 6.46°±0.10°, 8.37°±0.10°, 9.79°±0.10°, 10.64°±0.10°, 12.91°±0.10°, 16.79°±0.10°, 17.51°±0.10°, 18.15°±0.10°, 19.65°±0.10°, 20.12°±0.10°, 21.62°±0.10°, 23.34°±0.10° and 25.79°±0.10°.

4. The method of claim 2, wherein the crystalline form is Form A that exhibits an X-ray powder diffraction (XRPD) pattern shown in FIG. 1.

5. The method of claim 1, wherein the crystalline form is Form B that exhibits an X-ray powder diffraction (XRPD) pattern with characteristic peaks expressed in degrees 2-theta at 10.21°±0.10°, 11.93°±0.10°, 13.22°±0.10°, 14.35°±0.10°, 18.56°±0.10°, 20.79°±0.10°, 23.24°±0.10° and 25.15°±0.10°.

6. The method of claim 5, wherein the crystalline form is Form B that exhibits an X-ray powder diffraction (XRPD) pattern with characteristic peaks expressed in degrees 2-theta at 10.21°±0.10°, 11.93°±0.10°, 13.22°±0.10°, 14.35°±0.10°, 15.02°±0.10°, 16.31°±0.10°, 17.66°±0.10°, 18.56°±0.10°, 20.06°±0.10°, 20.79°±0.10°, 21.42°±0.10°, 23.24°±0.10°, 25.15°±0.10°, 26.21°±0.10°, 26.74°±0.10° and 29.44°±0.10°.

7. The method of claim 5, wherein the crystalline form is Form B that exhibits an X-ray powder diffraction (XRPD) pattern shown in FIG. 4.

8. The method of claim 1, wherein the crystalline Form B is a hydrate of compound (I).

9. The method of claim 1, wherein the crystalline form is Form C that exhibits an X-ray powder diffraction (XRPD) pattern with characteristic peaks expressed in degrees 2-theta at 8.41°±0.10°, 19.21°±0.10°, 20.49°±0.10°, 20.83°±0.10°, 21.69°±0.10°, 21.99°±0.10° and 22.13°±0.10°.

10. The method of claim 9, wherein the crystalline form is Form C that exhibits an X-ray powder diffraction (XRPD) pattern with characteristic peaks expressed in degrees 2-theta at 8.41°±0.10°, 13.71°±0.10°, 14.95°±0.10°, 17.01°±0.10°, 19.21°±0.10°, 20.49°±0.10°, 20.83°±0.10°, 21.46°±0.10°, 21.69°±0.10°, 21.99°±0.10°, 22.13°±0.10°, 24.95°±0.10°, 25.85°±0.10°, 26.63°±0.10° and 27.34°±0.10°.

11. The method of claim 9, wherein the crystalline form is Form C that exhibits an X-ray powder diffraction (XRPD) pattern shown in FIG. 7.

12. The method of claim 1, wherein the crystalline form is Form D that exhibits an X-ray powder diffraction (XRPD) pattern with characteristic peaks expressed in degrees 2-theta at 7.79°±0.10°, 10.18°±0.10°, 11.15°±0.10°, 12.40°±0.10°, 18.68°±0.10°, 20.43°±0.10° and 24.83°±0.10°.

13. The method of claim 12, wherein the crystalline form is Form D that exhibits an X-ray powder diffraction (XRPD) pattern with characteristic peaks expressed in degrees 2-theta at 7.79°±0.10°, 10.18°±0.10°, 11.15°±0.10°, 12.40°±0.10°, 12.90°±0.10°, 18.68°±0.10°, 19.73°±0.10°, 20.16°±0.10°, 20.43°±0.10°, 21.16°±0.10°, 23.14°±0.10°, 23.93°±0.10°, 24.83°±0.10°, 25.71°±0.10° and 27.11°±0.10°.

14. The method of claim 12, wherein the crystalline form is Form D that exhibits an X-ray powder diffraction (XRPD) pattern shown in FIG. 11.

15. The method of claim 1, wherein the crystalline form is Form E that exhibits an X-ray powder diffraction (XRPD) pattern with characteristic peaks expressed in degrees 2-theta at 5.96°±0.10°, 8.32°±0.10°, 9.34°±0.10°, 11.82°±0.10°, 15.09°±0.10°, 19.44°±0.10° and 25.60°±0.10°.

16. The method of claim 15, wherein the crystalline form is Form E that exhibits an X-ray powder diffraction (XRPD) pattern with characteristic peaks expressed in degrees 2-theta at 5.96°±0.10°, 8.32°±0.10°, 9.34°±0.10°, 11.82°±0.10°, 13.22°±0.10°, 15.09°±0.10°, 16.90°±0.10°, 17.46°±0.10°, 19.44°±0.10°, 21.08°±0.10°, 22.59°±0.10°, 23.12°±0.10°, 25.25°±0.10°, 25.60°±0.10° and 28.34°±0.10°.

17. The method of claim 15, wherein the crystalline form is Form E that exhibits an X-ray powder diffraction (XRPD) pattern shown in FIG. 14.

18. The method of claim 15, wherein the crystalline Form E is a mono acetate salt of compound (I).

19. The method of claim 1, wherein the crystalline form is Form F that exhibits an X-ray powder diffraction (XRPD) pattern with characteristic peaks expressed in degrees 2-theta at 10.27°±0.10°, 12.38°±0.10°, 18.59°±0.10°, 19.91°±0.10°, 20.14°±0.10°, 23.93°±0.10° and 24.78°±0.10°.

20. The method of claim 19, wherein the crystalline form is Form F that exhibits an X-ray powder diffraction (XRPD) pattern with characteristic peaks expressed in degrees 2-theta at 8.32°±0.10°, 10.27°±0.10°, 12.38°±0.10°, 13.05°±0.10°, 16.58°±0.10°, 18.01°±0.10°, 18.59°±0.10°, 19.70°±0.10°, 19.91°±0.10°, 20.14°±0.10°, 22.01°±0.10°, 23.56°±0.10°, 23.93°±0.10°, 24.78°±0.10° and 26.39°±0.10°.

21. The method of claim 19, wherein the crystalline form is Form F that exhibits an X-ray powder diffraction (XRPD) pattern shown in FIG. 15.

22. The method of claim 1, wherein the crystalline Form F is a mono maleic salt of compound (I).

* * * * *